(12) United States Patent
Hirahara

(10) Patent No.: US 7,568,309 B2
(45) Date of Patent: Aug. 4, 2009

(54) METHOD AND SYSTEM FOR PRODUCING MANUFACTURED SEEDS

(75) Inventor: Edwin Hirahara, Federal Way, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 135 days.

(21) Appl. No.: 11/091,326

(22) Filed: Mar. 28, 2005

(65) Prior Publication Data

US 2006/0032121 A1    Feb. 16, 2006

Related U.S. Application Data

(60) Provisional application No. 60/584,210, filed on Jun. 30, 2004.

(51) Int. Cl.
*A01C 1/06*    (2006.01)
(52) U.S. Cl. ........................................................ 47/57.6
(58) Field of Classification Search ................... 47/57.6
See application file for complete search history.

(56) References Cited

U.S. PATENT DOCUMENTS

| | | | |
|---|---|---|---|
| 2,309,702 A | 2/1943 | Kirschenbaum |
| 2,502,809 A | 4/1950 | Vogelsang |
| 2,809,772 A | 10/1957 | Weisz |
| 3,098,320 A | 7/1963 | Estkowski |
| 3,545,129 A | 12/1970 | Schreiber et al. |
| 3,688,437 A | 9/1972 | Hamrin |
| 3,690,034 A | 9/1972 | Knapp |
| 3,734,987 A | 5/1973 | Hamrin |
| 3,850,753 A | 11/1974 | Chibata et al. |
| 4,147,930 A | 4/1979 | Browne et al. |
| 4,166,006 A | 8/1979 | Hertl et al. |
| 4,252,827 A | 2/1981 | Yokoyama et al. |
| 4,465,017 A | 8/1984 | Simmons |
| 4,562,663 A | 1/1986 | Redenbaugh |
| 4,583,320 A | 4/1986 | Redenbaugh |
| 4,615,141 A | 10/1986 | Janick et al. |
| 4,628,633 A | 12/1986 | Nilsson |
| 4,665,648 A | 5/1987 | Branco et al. |

(Continued)

FOREIGN PATENT DOCUMENTS

CA    1241552    9/1988

(Continued)

OTHER PUBLICATIONS

Cheng, Z., and P.P. Ling, "Machine Vision Techniques for Somatic Coffee Embryo Morphological Feature Extraction," American Society of Agricultural Engineers 37(5):1663-1669, 1994.

(Continued)

*Primary Examiner*—Francis T Palo
(74) *Attorney, Agent, or Firm*—Christensen O'Connor Johnson Kindness PLLC

(57) ABSTRACT

A method of manufacturing an artificial seed (20) is provided. The method includes transporting a seed shell (22) to a media fill station (300) and depositing media (26) into the seed shell. The method also includes sealing (28) the media within one end of the seed shell, depositing an embryo (42) within the seed shell, and sealing (44) the embryo within the seed shell.

9 Claims, 15 Drawing Sheets

U.S. PATENT DOCUMENTS

| | | | |
|---|---|---|---|
| 4,715,143 A | 12/1987 | Redenbaugh et al. | |
| 4,769,945 A * | 9/1988 | Motoyama et al. | 47/57.6 |
| 4,777,762 A | 10/1988 | Redenbaugh et al. | |
| 4,777,907 A | 10/1988 | Sänger | |
| 4,779,376 A | 10/1988 | Redenbaugh | |
| 4,780,987 A | 11/1988 | Nelsen et al. | |
| 4,802,305 A | 2/1989 | Kojimoto et al. | |
| 4,802,905 A | 2/1989 | Spector | |
| 4,806,357 A | 2/1989 | Garrett et al. | |
| 4,808,430 A | 2/1989 | Kouno | |
| 4,866,096 A | 9/1989 | Schweighardt | |
| 4,879,839 A | 11/1989 | Gago et al. | |
| 5,010,685 A | 4/1991 | Sakamoto et al. | |
| 5,044,116 A | 9/1991 | Gago et al. | |
| 5,181,259 A | 1/1993 | Rorvig | |
| 5,183,757 A | 2/1993 | Roberts | |
| 5,236,469 A | 8/1993 | Carlson et al. | |
| 5,250,082 A | 10/1993 | Teng et al. | |
| 5,258,132 A | 11/1993 | Kamel et al. | |
| 5,284,765 A | 2/1994 | Bryan et al. | |
| 5,427,593 A | 6/1995 | Carlson et al. | |
| 5,451,241 A | 9/1995 | Cartson et al. | |
| 5,464,769 A | 11/1995 | Attree et al. | |
| 5,529,597 A | 6/1996 | Iijima | |
| 5,564,224 A | 10/1996 | Carlson et al. | |
| 5,565,355 A | 10/1996 | Smith | |
| 5,666,762 A | 9/1997 | Carlson et al. | |
| 5,680,320 A | 10/1997 | Helmer et al. | |
| 5,687,504 A | 11/1997 | Carlson et al. | |
| 5,701,699 A * | 12/1997 | Carlson et al. | 47/57.6 |
| 5,732,505 A | 3/1998 | Carlson et al. | |
| 5,771,632 A | 6/1998 | Liu et al. | |
| 5,784,162 A | 7/1998 | Carib et al. | |
| 5,799,439 A | 9/1998 | MacGregor | |
| 5,821,126 A | 10/1998 | Durzan et al. | |
| 5,842,150 A | 11/1998 | Renberg et al. | |
| 5,877,850 A | 3/1999 | Ogata | |
| 5,902,398 A * | 5/1999 | Kohno et al. | 118/23 |
| 5,930,803 A | 7/1999 | Becker et al. | |
| 5,960,435 A | 9/1999 | Rathmann et al. | |
| 6,021,220 A | 2/2000 | Anderholm | |
| 6,092,059 A | 7/2000 | Straforini et al. | |
| 6,119,395 A | 9/2000 | Hartle et al. | |
| 6,145,247 A | 11/2000 | McKinnis | |
| 6,470,623 B1 * | 10/2002 | Hirahara | 47/57.6 |
| 6,557,298 B2 | 5/2003 | Obert et al. | |
| 6,567,538 B1 | 5/2003 | Pelletier | |
| 6,582,159 B2 | 6/2003 | McKinnis | |
| 6,684,564 B1 * | 2/2004 | Hirahara | 47/57.6 |
| 7,131,234 B2 | 11/2006 | Carlson et al. | |
| 7,168,205 B2 | 1/2007 | Hartle et al. | |
| 7,289,646 B2 | 10/2007 | Hirahara et al. | |
| 7,530,197 B2 | 5/2009 | Timmis et al. | |
| 2002/0192686 A1 | 12/2002 | Adorjan et al. | |
| 2003/0055615 A1 | 3/2003 | Zhang et al. | |
| 2004/0266889 A1 | 12/2004 | Hirahara | |
| 2004/0268445 A1 | 12/2004 | Carlson et al. | |
| 2005/0108929 A1 * | 5/2005 | Hirahara | 47/1.01 R |
| 2005/0108935 A1 * | 5/2005 | Hirahara | 47/57.6 |
| 2005/0108937 A1 * | 5/2005 | Hirahara | 47/57.6 |
| 2005/0114918 A1 * | 5/2005 | Hirahara et al. | 800/278 |
| 2005/0133528 A1 * | 6/2005 | Hirahara | 222/1 |
| 2006/0032121 A1 * | 2/2006 | Hirahara | 47/57.6 |
| 2006/0070145 A1 * | 3/2006 | Carlson et al. | 800/298 |

FOREIGN PATENT DOCUMENTS

| | | |
|---|---|---|
| CA | 1250296 | 2/1989 |
| EP | 0 107 141 A1 | 5/1984 |
| EP | 0 300 730 A1 | 1/1989 |
| EP | 0 380 692 A1 | 8/1990 |
| EP | 0776601 A1 | 6/1997 |
| FR | 2 680 951 A1 | 3/1993 |
| JP | 61040708 | 2/1986 |
| JP | 62275604 | 11/1987 |
| JP | 63133904 | 6/1988 |
| JP | 63152905 | 6/1988 |
| JP | 2-46240 | 2/1990 |
| JP | 407179683 A | 7/1995 |
| JP | 10327611 | 12/1998 |
| JP | 10327612 | 12/1998 |
| NZ | 539693 A * | 9/2006 |
| WO | WO 91/00781 A1 | 1/1991 |
| WO | WO 91/01803 | 2/1991 |
| WO | WO 92/07457 A1 | 5/1992 |
| WO | WO 95/05064 | 2/1995 |
| WO | WO 98/33375 | 8/1998 |
| WO | WO 99/26470 | 6/1999 |
| WO | 013701 | 3/2001 |

OTHER PUBLICATIONS

Chi, C.-M., et al., "An Advanced Image Analysis System for Evaluation of Somatic Embryo Development," Biotechnology and Bioengineering 50:65-72, Apr. 1996.

Dupuis, J.-M., et al., "Pharmaceutical Capsules as a Coating System for Artificial Seeds," Bio/Technol. 12:385-389, 1994.

Ibarbia, E.A., "Synthetic Seed: Is it the Future," Western Grower and Shipper 59:12, 1998.

Janick, J., "Production of Synthetic Seed Via Desiccation and Encapsulation" (Abstract), In Vitro 24(3, Part 2):70A, 1989.

Kim, Yong-Hwan and J. Janick, "ABA and Polyox-Encapsulation or High Humidity Increases Survival of Desiccated Somatic Embryos of Celery," HortScience 24(4):674-676, 1989.

Kitto, S.L., and J. Janick, "A Citrus Embryo Assay to Screen Water-Soluble Resins as Synthetic Seed Coats," HortScience 20(1):98-100, 1985.

Kitto, S.L., and J. Janick, "Production of Synthetic Seeds by Encapsulating Asexual Embryos of Carrot," J. Amer. Soc. Hort. Sci. 110(2):277-282, 1985.

Li, X.-Q., "Somatic Embryogenesis and Synthetic Seed Technology Using Carrot as a Model System," in K. Redenbaugh (ed.), Synseeds: Applications of Synthetic Seeds to Crop Improvement, CRC Press, Inc., Boca Raton, Fla., 1993, pp. 289-304.

Redenbaugh, K., et al., "Encapsulated Plant Embryos," Biotechnology in Agriculture, 1998, pp. 225-248.

Redenbaugh, K., et al., "Encapsulation of Somatic Embryos for Artificial Seed Production" (Abstract), In Vitro 20 (2):256-257, 1984.

Redenbaugh, K., et al., "Encapsulation of Somatic Embryos in Synthetic Seed Coats," HortScience 22(5):803-809, 1987.

Redenbaugh, K., et al., "III.3 Artificial Seeds—Encapsulated Somatic Embryos," Biotech. in Agr. & Far. 17:395-416, 1991.

Redenbaugh, K., et al., "Scale-Up: Artificial Seeds," in Green et al. (eds.), Plant Tissue and Cell Culture, Alan R. Liss, Inc., New York, 1987, pp. 473-493.

Redenbaugh, K., et al., "Somatic Seeds: Encapsulation of Asexual Plant Embryos," Bio/Technology 4:797-801, 1986.

Rogers, M., "Synthetic-Seed Technology," Newsweek, Nov. 28, 1983.

Sanada, M., et al., "Celery and Lettuce," in M.K. Redenbaugh (ed.), Synseeds: Applications of Synthetic Seeds to Crop Improvement, CRC Press, Inc., Boca Raton, Fla., 1993, pp. 305-322.

Senaratna, T., "Artificial Seeds," Biotech Adv. 10(3)379-392, 1992.

Stuart, D.A., and M.K. Redenbaugh, "Use of Somatic Embryogenesis for the Regeneration of Plants," in H.M. LeBaron et al. (eds.), Biotechnology in Agricultural Chemistry, American Chemical Society, Washington, D.C., 1987, pp. 87-96.

Teasdale, R.D., and P.A. Buxton, "Culture of Pinus Radiata Embryos with Reference to Artificial Seed Production," New Zealand J. For Sci. 16(3):387-391, 1986.

* cited by examiner

METHOD AND SYSTEM FOR PRODUCING MANUFACTURED SEEDS

CROSS REFERENCE TO RELATED APPLICATION

The present application claims the benefit of U.S. Provisional Application No. 60/584,210, filed Jun. 30, 2004.

FIELD OF THE INVENTION

The present invention relates generally to artificial seeds and, more particularly to, a method and system of producing manufactured seeds.

BACKGROUND OF THE INVENTION

Asexual propagation for plants has been shown for some species to yield large numbers of genetically identical embryos, each having the capacity to develop into a normal plant. Such embryos must usually be further cultured under laboratory conditions until they reach an autotrophic "seedling" state characterized by an ability to produce their own food via photosynthesis, resist desiccation, produce roots able to penetrate soil, and fend off soil microorganisms. Some researchers have experimented with the production of artificial seeds, known as manufactured seeds, in which individual plant somatic or zygotic embryos are encapsulated in a seed coat. Examples of such manufactured seeds are disclosed in U.S. Pat. No. 5,701,699, issued to Carlson et al., the disclosure of which is hereby expressly incorporated by reference.

Typical manufactured seeds include a seed shell, synthetic gametophyte and a plant embryo. A manufactured seed that does not include the plant embryo is known in the art as a "seed blank." The seed blank typically is a cylindrical capsule having a closed end and an open end. The synthetic gametophyte is placed within the seed shell to substantially fill the interior of the seed shell. A longitudinally extending hard porous insert, commonly known as a cotyledon restraint, may be centrally located within the synthetic gametophyte and includes a centrally located cavity extending partially through the length of the cotyledon restraint. The cavity is sized to receive the plant embryo therein. The well-known plant embryo includes a radicle end and a cotyledon end. The plant embryo is deposited within the cavity of the cotyledon restraint cotyledon end first and is sealed within the seed blank by at least one end seal. There is a weakened spot in the end seal to allow the radicle end of the embryo to penetrate the end seal.

Currently, the seed shell is manufactured by hand and is formed from sectioning a tube, such as a straw, and processing the sections of the tube to enhance its abilities to withstand exposure to the environment. One such seed shell is manufactured by sectioning a straw of fibrous material, and then coating the resulting straw section with a wax. One suitable method for applying the wax coating is to dip the straw sections into a bath of wax. The straw sections are then withdrawn from the wax bath and then the wax is permitted to harden to seal the straw sections.

Delivery of the plant embryo within the seed coat has utilized a liquid-based transport system to move the plant embryo through the manufactured seed production line. In such a liquid-based transport system, plant embryos are placed in a container of liquid to orient them in a like direction. The plant embryos are caused to float to the top of the container, such that each embryo floats upwardly within the container cotyledon end first. From the top of the container, additional liquid is used to propel the plant embryos out of the container while maintaining their cotyledon end first orientation. Liquid is then used to transport the plant embryos through the remaining manufactured seed production line steps. The embryos are hand selected and inserted into the seed coat. Thereafter, the embryo is sealed within the seedcoat resulting in a manufactured seed suitable for planting.

Although such manufacturing systems are effective at producing manufactured seeds, they are not without their problems. As a non-limiting example, because such manufacturing systems are predominately human controlled, they are expensive, labor intensive, and relatively slow at mass producing manufactured seeds.

Thus, there exists a need for a method and system of producing manufactured seeds that is capable of reliably producing a large number of manufactured seeds at a relatively low cost, and minimizing the risk of damaging or contaminating the plant embryo.

SUMMARY OF THE INVENTION

In a material handling system having means for automatically assembling and transporting an artificial seed between a plurality of assembly stations arranged in a substantially sequential configuration, a method of manufacturing an artificial seed is provided. The method includes transporting a seed shell to a media fill station and depositing media into the seed shell. The method also includes sealing the media within one end of the seed shell, depositing an embryo within the seed shell, and sealing the embryo within the seed shell. In accordance with another embodiment of the present invention, the method further includes coupling a seed shell with a restraint prior to transporting a seed shell to a media fill station. Another embodiment also includes placing a restraint on a receptacle prior to coupling a seed shell with a restraint. In still yet another embodiment, the method also includes causing the media to change state.

A material handling system for automatically assembling and transporting an artificial seed between a plurality of assembly stations arranged in a sequential configuration is also provided. The material handling system includes a transport assembly having means for selectively restraining and transporting seed shells, and a media fill station in selective communication with the transport assembly. The material handling system also includes a first end seal formation station in selective communication with the transport assembly, and an embryo delivery station in selective communication with the transport assembly.

In yet another embodiment of the present invention, the material handling system includes a second end seal formation station in selective communication with the transport assembly. Further, a cooler in communication with the transport assembly to cool a seed shell is also suitably part of another embodiment of the present invention.

The method and system of manufacturing an artificial seed formed in accordance with the various embodiments of the present invention have several advantages over currently available methods. The method and system of the present disclosure is simpler to operate, as it consolidates various parts of the assembly procedure at substantially one location. Also, because such a method and system is automated, it reduces manual labor required to manipulate and assemble artificial seeds and, therefore is cheaper than existing systems.

Thus, a method and system of manufacturing artificial seeds in accordance with the various embodiments of the present invention has a high degree of reliability, and is capable of mass producing artificial seeds at a relatively low cost.

BRIEF DESCRIPTION OF THE DRAWINGS

The foregoing aspects and many of the attendant advantages of this invention will become better understood by reference to the following detailed description, when taken in conjunction with the accompanying drawings, wherein.

DETAILED DESCRIPTION OF THE PREFERRED EMBODIMENT

Figure 1:
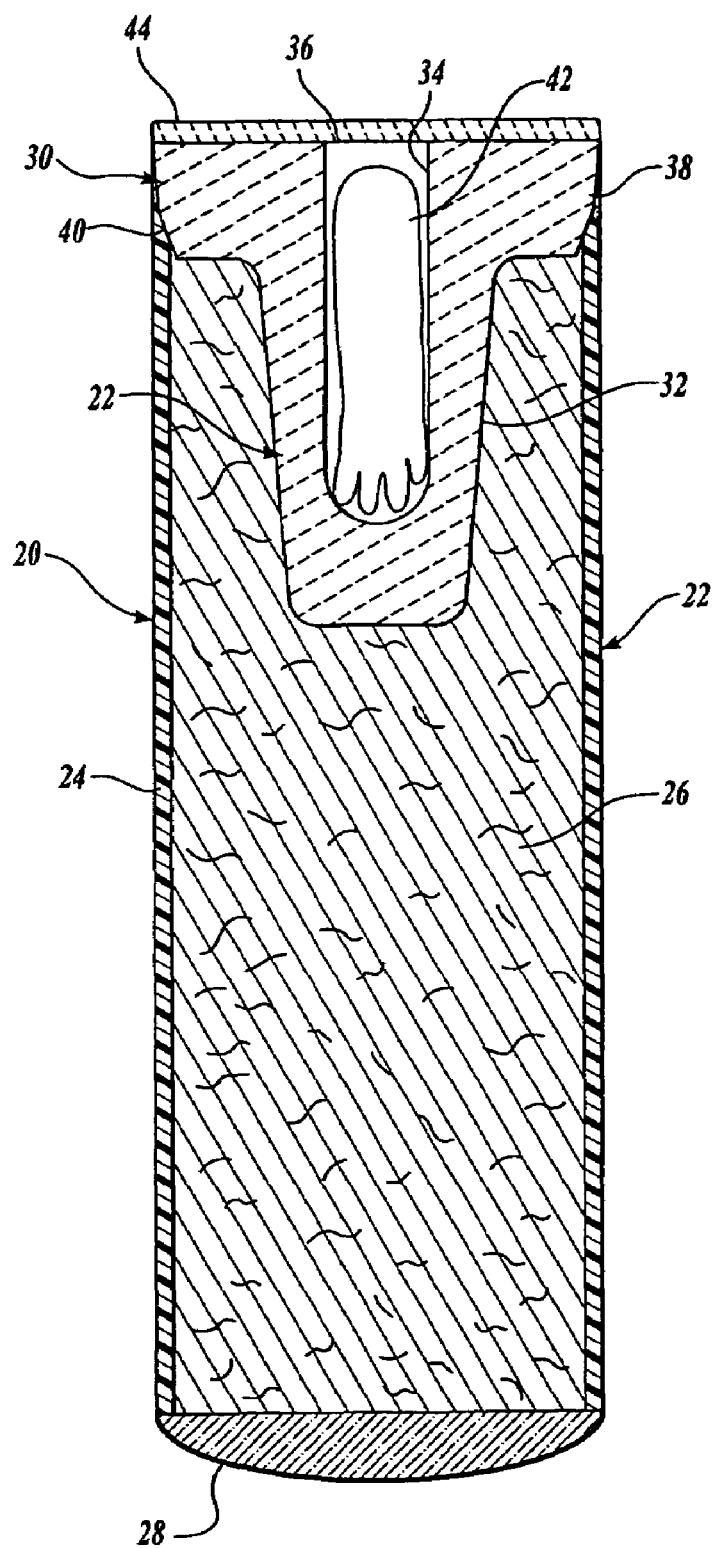
FIG. 1 is a manufactured seed formed in accordance with one embodiment of the present invention.

FIG. 1 illustrates a manufactured seed 20 constructed in accordance with certain embodiments of the present invention. The manufactured seed 20 includes a cylcap 22, a seed shell 24, a nutritive media 26, such as a gametophyte, and a dead end seal 28. The seed shell 24 is suitably formed from a section of tubular material. In one embodiment, the seed shell 24 is a sectioned straw of fibrous material, such as paper. The sections of straw may be pre-treated in a suitable coating material, such as wax. In other embodiments, the seed shell 24 is formed from a section of biodegradable, plastic material. It should be apparent that although sectioning tubes is preferred, other embodiments, such as obtaining tubes of appropriate size for use as manufactured seeds, are also within the scope of the present invention.

The cylcap 22 is suitably manufactured from a porous material having a hardness strong enough to resist puncture or fracture by a germinating embryo, such as a ceramic material, and includes an end seal portion 30 and a cotyledon restraint portion 32. The cotyledon restraint portion 32 is suitably integrally or unitarily formed with the end seal portion 30. The cylcap 22 also includes a longitudinally extending cavity 34 extending through the end seal portion 30 and partially through one end of cotyledon restraint portion 32. The open end of the cavity 34 is known as a cotyledon restraint opening 36. The cavity 34 is sized to receive a plant embryo (not shown) therein.

In certain embodiments, as the cylcap 22 is suitably manufactured from a porous material, it may be desirable to coat the cylcap 22 with a barrier material to reduce the rate of water loss and restrict or reduce microbial entry. Such barriers include wax, polyurethane, glaze, nail polish, and a coating sold by Airproducts Airflex 4514.

The end seal portion 30 is suitably circular when viewed in a top planar view and includes sidewalls 38. Although circular is the preferred embodiment of the end seal portion 30, other embodiments and shapes, such as polygonal, square, triangular, oval and other shapes, are also within the scope of the present invention.

In the embodiment of FIG. 1, the sidewalls 38 are defined by the thickness of the end seal portion 30 and has a diameter substantially equal to the inside diameter of the seed shell 24. In certain embodiments, the cylcap 22 is bonded to the seed shell 24 by heat. As a non-limiting example, during manufacturing, the cylcap 22 may be heated to a pre-determined temperature, such that when the seed shell 24 and the cylcap 22 are co-joined, heat transferred between the cylcap 22 and the seed shell 24 causes either the seed shell 24, the cylcap 22, or both to melt, thereby bonding the two together. Other methods of bonding the cylcap 22 to the seed shell 24, such as a wax bond or a hot glue melt, are also within the scope of the present invention.

As may be best seen by referring to FIG. 1, the sidewalls 38 may include a tapered portion 40. The tapered portion 40 may be a chamfer of one end of the end seal portion 30. The tapered portion 40 assists in assembling the cylcap 22 to the seed coat 24 during manufacturing. Although a tapered portion 40 is preferred, other embodiments, such as a cylcap that does not include a tapered portion, are also within the scope of the present invention. An embryo 42 is disposed within the cavity 34 and is suitably sealed therein by a live end seal 44.

A method and system of manufacturing a manufactured seed 20 in accordance with the current embodiment of the present invention will now be described in greater detail. A material handling system 60 for automatically assembling and transporting manufactured seeds 20 between a plurality of assembly stations is best seen by referring to FIG. 2. The material handling system 60 includes a transport assembly 100, a cylcap and seed shell coupler assembly 200, and a combination media dispenser and cooler assembly 300. The material handling system 60 also includes a dead end seal formation assembly 400, an embryo delivery system 500, a live end seal formation assembly 600, and a manufactured seed removal assembly 700.

The transport assembly 100 includes a carousel 110 operatively connected to a drive assembly 112 by a spindle shaft 114 extending through a platform 116. The drive assembly 112 is suitably a well-known motor, such as a stepper motor or a well known AC or DC motor. The spindle shaft 114 is suitably a rod extending between the drive assembly 112 and a holder plate 118. The spindle shaft 114 is coupled to the holder plate 118 by a well known bearing (not shown).

Disposed around the perimeter of the holder plate 118 is a plurality of arms 120 extending radially outwards from the holder plate 118. Attached at the ends of each arm 120 is a clamp 122. The clamps 122 are selectively operable to secure and release a manufactured seed 20 between the various stations of the materials handling system 60. As coupled to the holding plate 118, the arms 120 are disposed in a substantially circular configuration. Although a substantially circular configuration of arms is preferred, other sequential configurations, such as an oval or substantially linear configuration, are also within the scope of the present invention.

Figure 2:
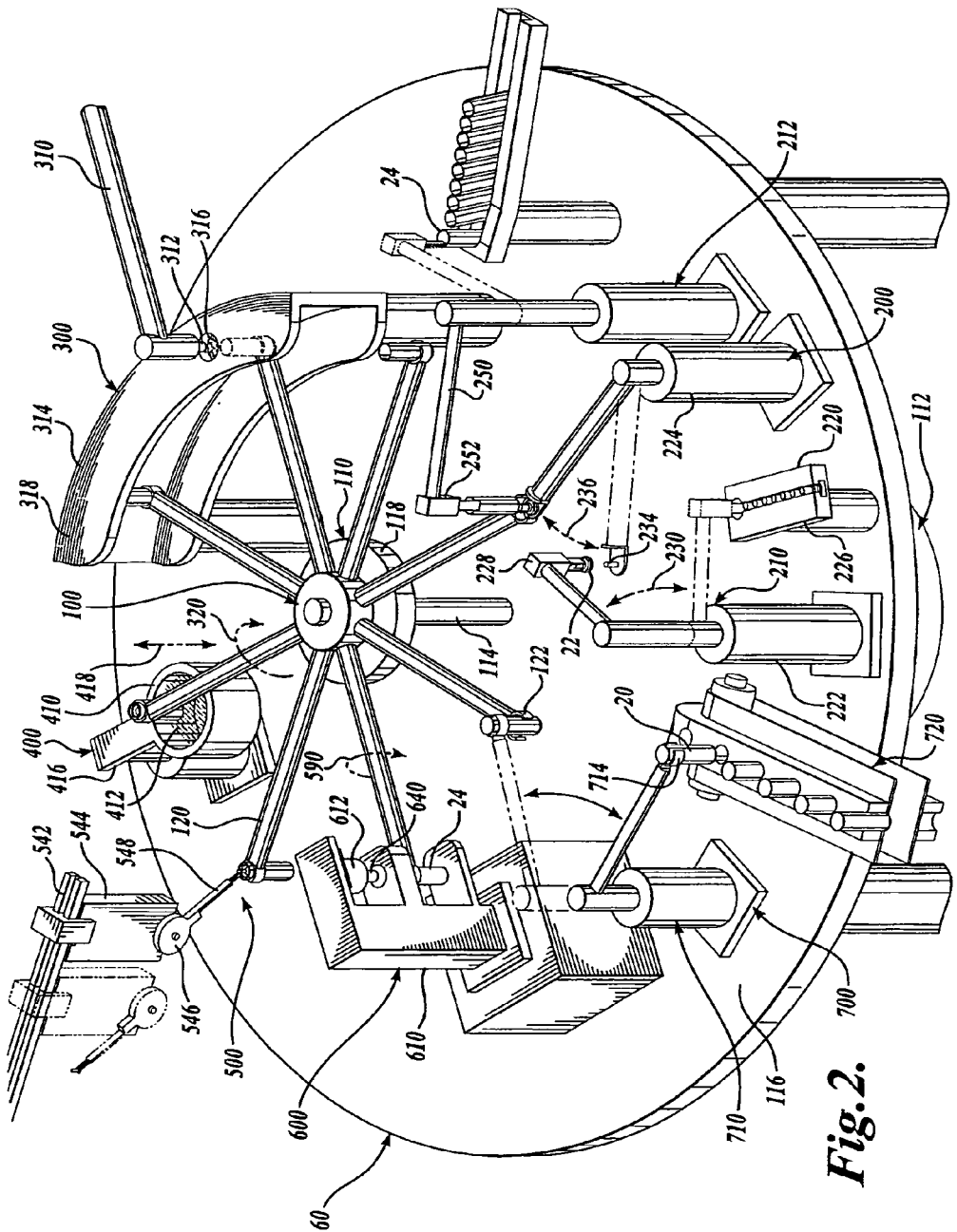
FIG. 2 is an isometric view of a materials handling system constructed in accordance with one embodiment of the present invention.
Figure 3:
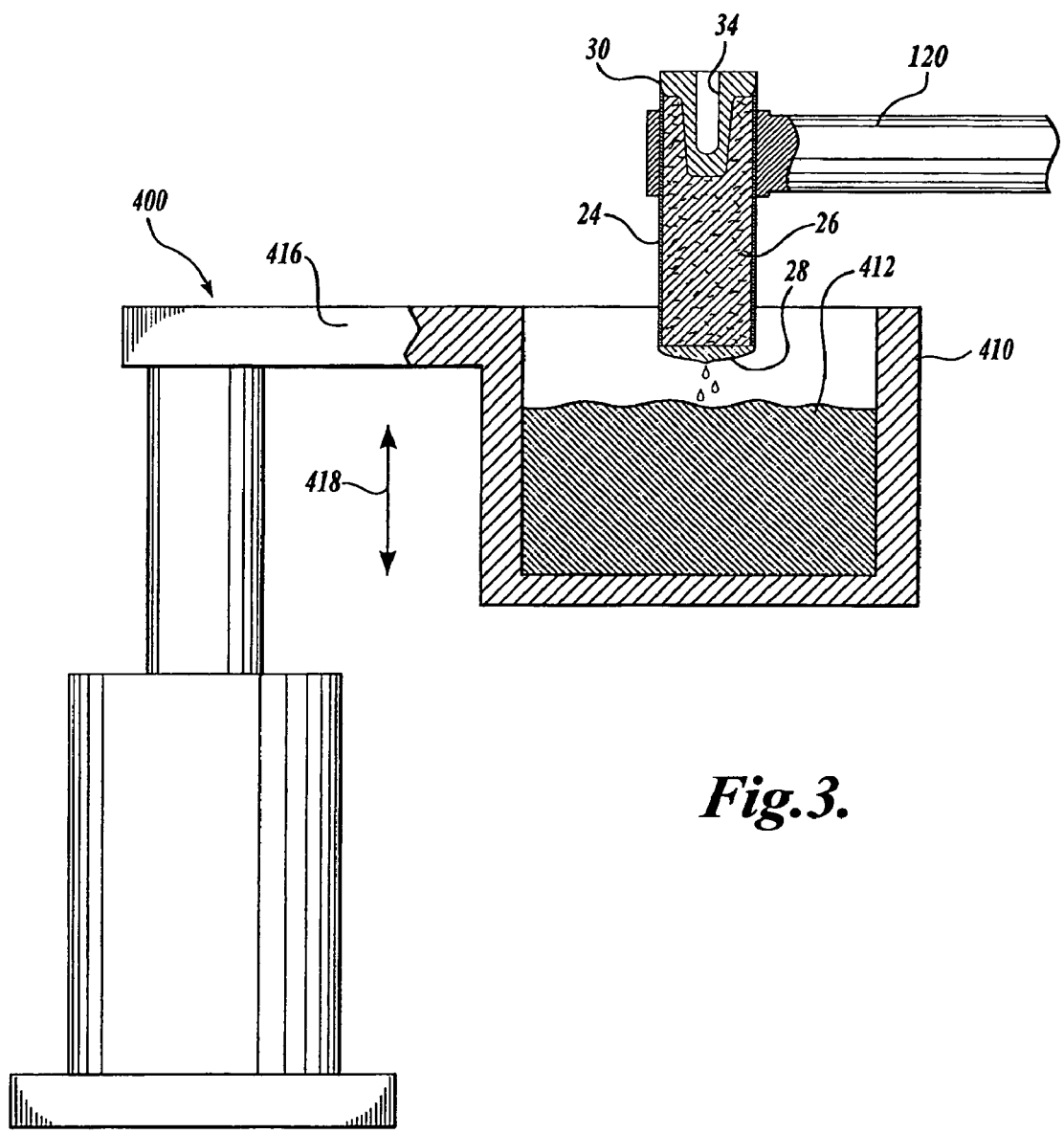
FIG. 3 is a dead end seal assembly of the materials handling system of FIG. 2.

Still referring to FIG. 2, the cylcap and seed shell coupler assembly 200 ("the coupler assembly 200") will now be described in greater detail. The coupler assembly 200 includes a cylcap handler assembly 210 and a seed shell handler assembly 212. The cylcap handler assembly 210 includes a feeder arm 220 and first and second robotic arms 222 and 224. The feeder arm 220 is suitably coupled to a reservoir (not shown) containing a plurality of cylcaps 22. The cylcaps 22 are stored within the reservoir and are fed onto the feeder arm 220, such that the cotyledon restraint portion 32 of the cylcap 22 is positioned upwards.

The feeder arm 220 includes a bridge 226 extending from the reservoir. The bridge 226 and reservoir are suitably, but not necessarily, heated to heat the cylcap 22 to a predetermined temperature. It is desirable that the cylcap 22 is heated, such that when the cylcap 22 is coupled to a seed shell, the cylcap 22 and seed shell are bonded together by heat fusion.

The first robotic arm 222 is suitably a hydraulically operated mechanism that includes a tweezer assembly 228 operatively connected to one end of the first robotic arm 222. The tweezer assembly 228 is operable to selectively retrieve a cylcap 22 from the bridge 226 and place it on a portion of the second robotic arm 224. The first robotic arm 222 is rotates between the bridge 226 and the second robotic arm 224 in the direction indicated by the arrow 230.

The second robotic arm 224 is suitably a hydraulically operated mechanism and includes a cylcap holder plate 232 connected to one end of the second robotic arm 224. The cylcap holder plate 232 includes an upwardly extending peg 234 sized to be inserted into the correspondingly shaped cavity 34 of the cylcap 22. The second robotic arm 224 is selectively rotated into communication with the seed shell handler assembly 212 and indicated by the arrow 236.

The seed shell handler assembly 212 includes an arm 250 having a tweezer assembly 252 operatively connected to one end of the arm 250. The tweezer assembly 252, like the tweezer assembly 228 of the first robotic arm 222, is suitably a controllable pickup device adapted to selectively retrieve seed shells 24 from a reservoir (not shown). The seed shell handler assembly 212 positions a seed shell 24 above the cylcap 22. As positioned, the arm 250 selectively displaces the seed shell 24 downwardly, such that the cylcap 22 is received within the seed shell 24. The tweezer assembly 252 then releases the seed shell 24, and the arm 252 raises upwardly and away from the now-joined cylcap 22 and seed shell 24. As noted above, the cylcap 22 and seed shell 24 are bonded together by heat fusion.

Although it is preferred that the arms 220 and 252 actuate downwardly to either retrieve a cylcap 22 or place the seed shell 24 into contact with a cylcap 22, it should be apparent that other methods, such as displacing other components of the materials handling system 60, are also within the scope of the present disclosure. It should also be apparent that although a material handling system 60 having both a cylcap handler assembly 210 and a seed shell handler assembly 212 is preferred, such assemblies are optional to the operation of such a system. As a nonlimiting example, a seed shell and cylcap may be preassembled at a location separate from the material handling system 60, such that a seed shell already including a cylcap disposed therein may be retrieved by the transport assembly 100 or an equivalent apparatus. Accordingly, such embodiments are also within the scope of the present invention.

The now coupled cylcap 22 and seed shell 24 is selectively retrieved from the cylcap and seed shell coupler assembly 200 by the clamp 122 of one of the arms 120 of the transport assembly 100. The partially assembly seed blank is transported to the combination media dispenser and cooler assembly 300.

The combination media dispenser and cooler assembly 300 includes a filler arm 310, a dispensing nozzle 312 in fluid communication with the filler arm 310, and a chiller 314. The filler arm 310 is operatively connected to a reservoir (not shown) containing liquid gametophyte. The dispensing nozzle 312 is suitably located above a bore 316 extending through a portion of the chiller 314. Although the present embodiment describes the dispensing nozzle 312 as located proximate to a bore 316 extending through the chiller 314, other embodiments, such as locating the dispensing nozzle 312 before the chiller 314, are also within the scope of the present invention.

When a seed shell 24 is located beneath the dispensing nozzle 312, a predetermined amount of gametophyte 26 is selectively dispensed into the open end of the seed shell 24. The exact amount of gametophyte 26 dispensed into the seed shell 24 varies according to the volume of the seed shell 24. In one preferred embodiment, the seed shell 24, including the cylcap 22, is filled with gametophyte 26 to a predetermined volume that is less than the total available volume after the cylcap 22 is disposed within the seed shell 24.

As a non-limiting example, the predetermined volume of gametophyte 26 disposed within the seed shell 24 is about 10 $mm^3$ to 50 $mm^3$ less than the total available volume of the seed shell 24 containing the cylcap 22. The exact volume is determined to permit attachment of the dead end seal 28 to the resulting manufactured seed 20. Accordingly, the predetermined amount of gametophyte 26 is a direct function of the size and shape of a seed shell 24 and, in certain embodiments, is less than the total volume available. After the predetermined amount of gametophyte 26 is dispensed into the seed shell 24 at this assembly station, the material handling system 60 selectively moves the seed shell 24 further within the chiller 314 of the combination media dispenser and cooler assembly 300.

The chiller 314 is a well-known chiller and only portions are shown for ease of description. The chiller 314 includes a chiller box 318 substantially encasing the seed shell 24 as it is moved through the combination media dispenser and cooler assembly 300. The chiller 314 accelerates a state change of gametophyte 26 within the seed shells 24. Specifically, the chiller 314 accelerates the rate by which the gametophyte 26 changes state from a substantially liquid state to a gelatin-like state. Also, the chiller 314 may assist in bonding the cylcap 22 within the seed shell 24 for those embodiments where the cylcap 22 and seed shell 24 are coupled together as part of the seed blank 20 manufacturing process.

Before gametophyte 26 is deposited within the seed shell 24, the seed shell 24 passes through a portion of the chiller 314, thereby accelerating the rate at which the seed shell 24 and cylcap 22 are bonded. Although it is preferred that the chiller 314 pre-cool the combination seed shell and cylcap, other embodiments, such as permitting the seed shell and cylcap bond under ambient conditions, are also within the scope of the present invention. After completion of the cooling stage, the combination of the seed shell 24, cylcap 22, and gametophyte 26 is commonly referred to as a "seed blank."

Although a plurality of arms 120 are illustrated as being disposed within the combination media dispenser and cooler assembly 300, other embodiments, such as only one arm 120 within the chiller box 130, are also within the scope of the present invention. Also, the combination media dispenser and cooler assembly 300 is an optional component of the material handling system 60 and, therefore, other embodiments, such as material handling systems that do not include such an assembly, are also within the scope of the present invention.

After the cooling cycle has been completed, the transport assembly 100 is selectively actuated to the dead end seal formation assembly 400. Before reaching or, alternatively, when the seed shell 24 is moved to the dead end seal formation assembly 400, the arm 120 rotates the seed shell 24 180°, as indicated by the arrow 320. The dead end seal formation assembly 400 includes a container 410 of an end seal formation material 412, such as wax. The container 410 is suitably connected to a dipping arm mechanism 416. The container 410 is a tub-like structure filled with the end seal formation material 412 and is suitably heated by a heating apparatus (not shown) to keep the end seal formation material 412 in a substantially liquid state.

The dipping arm mechanism 416 is a pneumatically or hydraulically actuated mechanism and is operable to displace the container 410 between a stowed position and a raised operable position, where one end of a pre-positioned seed shell 24 is partially submerged within the container 410. This is substantially indicated by the arrow 418.

In the raised position, an open end (not shown) of the seed shell 24 is immersed within the end seal formation material 412 for a predetermined period of time. The predetermined period of time, end seal formation material 412 used, and temperature of the end seal formation material 412 when it is disposed within the container 410, all affect the shape and thickness of the resulting dead end seal 28. Each of the foregoing parameters may be varied to control the shape and thickness of the dead end seal 28.

As a non-limiting example, if the seed shell 24 is soaked in the end seal formation material 412 for a period of time exceeding the time it takes for the end seal formation material 412 to adhere to the open end of the seed shell 24, the end seal formation material 412 flows off the end of the end of the seed shell 24 to create a nipple-like protrusion.

The length of time the seed shell 24 is immersed within the container 410 is determined by observation. Specifically, after the seed shell 24 is removed from the container 410, the resulting dead end seal 28 is observed to ensure that a proper seal between the dead end seal 28 and the seed shell 24 has been formed. In certain embodiments of the present disclosure, the predetermined period of time may range between 0.1 seconds and 50 seconds, or longer. In another embodiment, the range is between 0.1 and 8 seconds. In still yet another embodiment, the seed shell 24 is immersed within the end seal formation material 412 in a range between 0.5 to 5 seconds. In yet another non-limiting example, the seed shell 24 is immersed in the end seal formation material 412 for one second. It should be apparent to one of ordinary skill that the soak time may be shorter or longer than those set forth above, and therefore, such times are also within the scope of the present invention.

It has been discovered that depending on how long the seed shell 24 is immersed within the end seal formation material 412, the depth to which the seed shell 24 is immersed within the end seal formation material 412, and the density and temperature of the end seal formation material 412, all combine to determine whether a dead end seal 28 is formed and also determines the shape of the dead end seal 28. Thus, adjusting various parameters, such as the time that the seed shell 24 is immersed within the end seal formation material 412, results in dead end seals 28 of varying thickness and shapes.

After the seed shell 24 has soaked within the end seal formation material 412 for the predetermined period of time, the seed shell 24 is removed from the container 410. The end seal formation material 412 then drips down and off the seed shell 24 and the remaining end seal formation material 412 hardens to seal the open end of the seed shell 24. The end seal formation material 412 forms a plug that is attached to both the sidewalls and the ends of the seed coats 24.

Referring to FIGS. 4-7, the embryo delivery assembly 500 will now be described in greater detail. As seen best by referring to FIG. 4, the embryo delivery system 500 includes an embryo orientation assembly 510 and a transfer assembly 512. The embryo delivery system 500 further includes a control system 514 having a computer 516 or other general computing device. The control system 514 sends and receives control signals to and from the assemblies 510 and 512 for automating the embryo delivery process.

Figure 5:
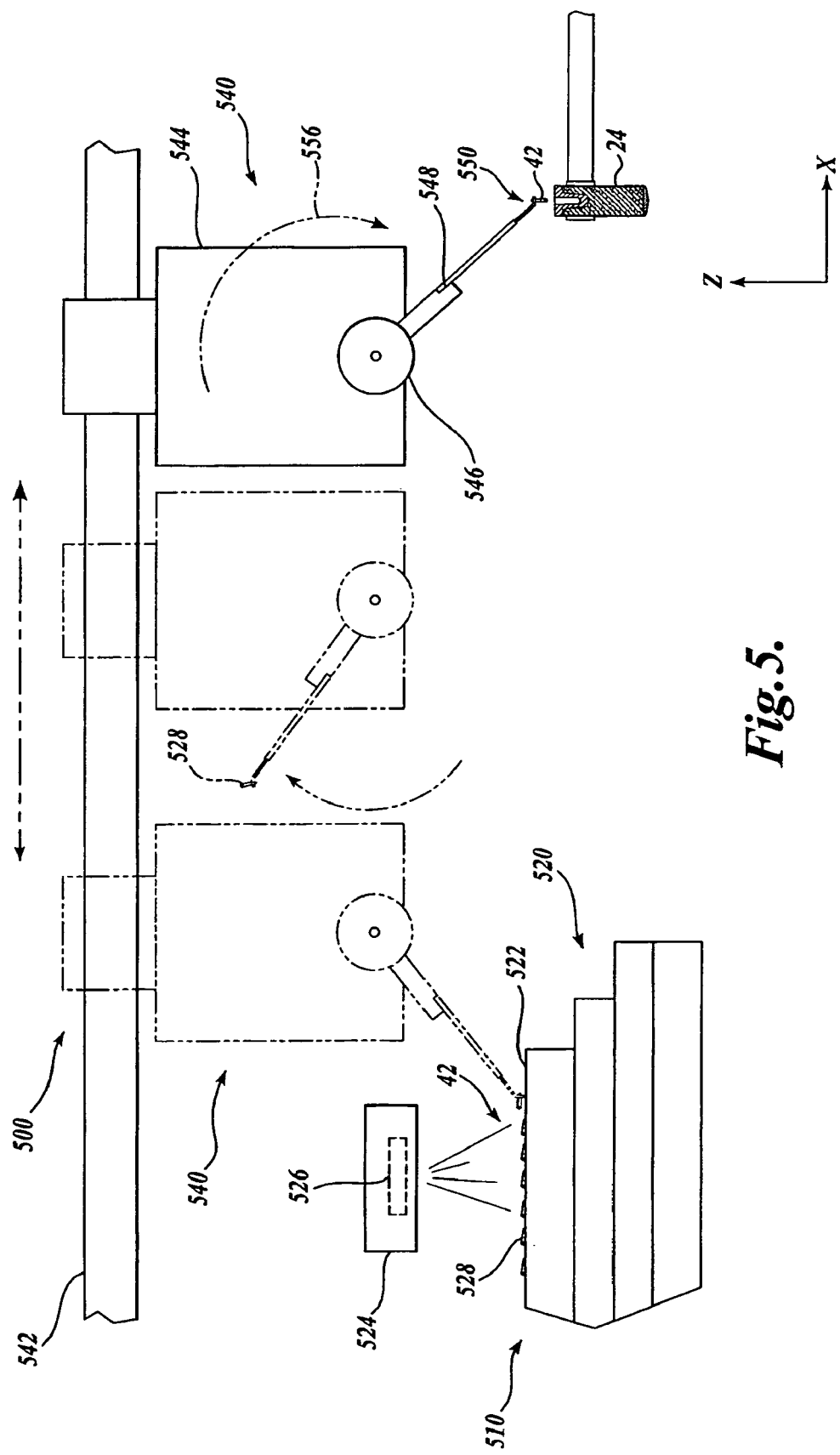
FIG. 5 is a partial side planar view of the embryo delivery system for the materials handling system of FIG. 2.
Figure 6:
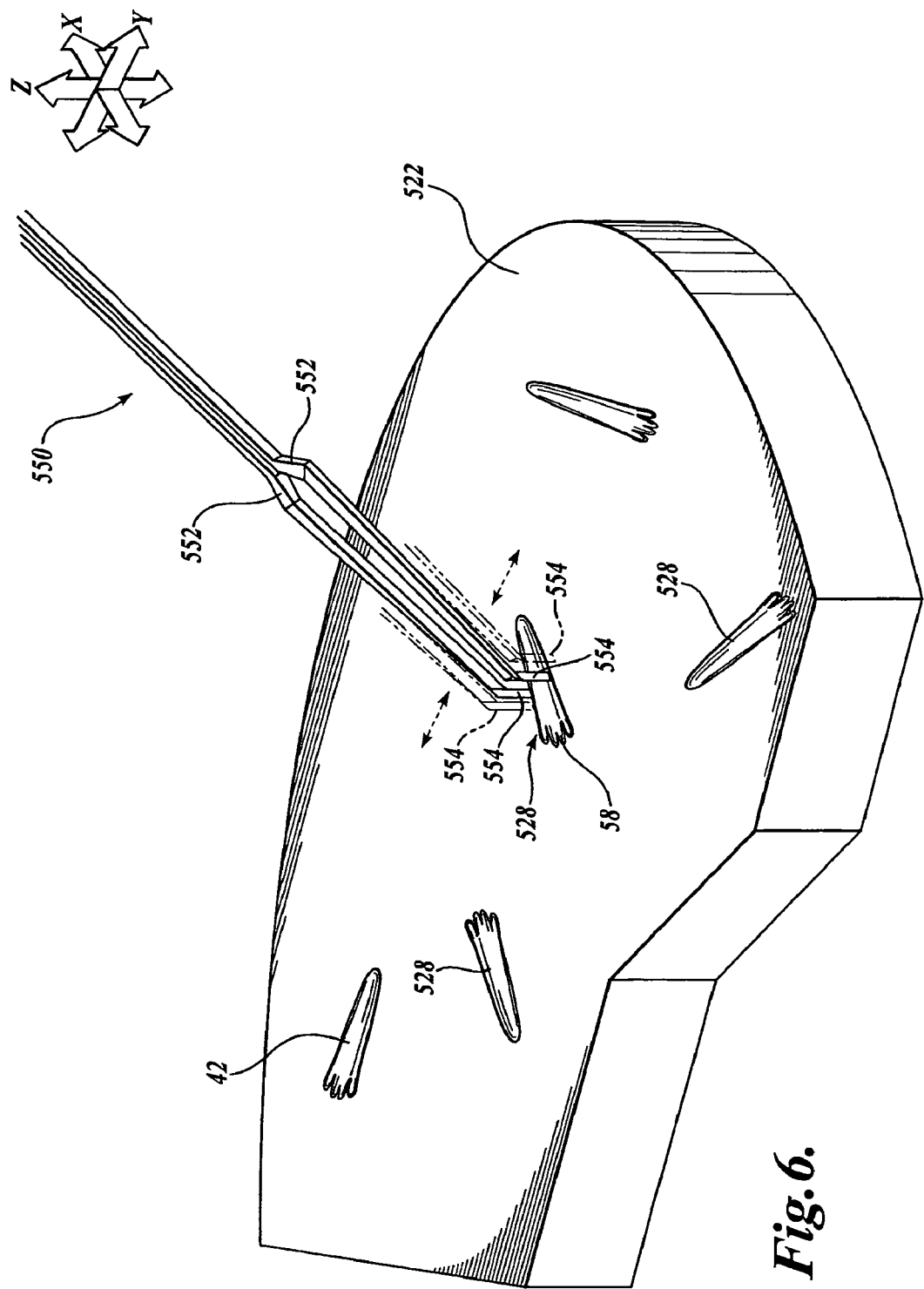
FIG. 6 is a partial perspective view of is a set of microtweezers from the embryo delivery system of FIG. 5, showing the microtweezers retrieving a qualified embryo.

Referring now to FIGS. 5 and 6, the embryo orientation assembly 510 will now be described in greater detail. The orientation assembly 510 includes a X-Y-rotation positioning table 520 ("positioning table 520"). The positioning table 520 selectively translates in two dimensions, and rotates about an axis orthogonal to the translating directions. In particular, the positioning table 520 is selectively positionable fore and aft along the X direction, side-to-side along the Y direction, as well as rotating about the Z-axis for affecting angular displacement. In one embodiment of the present invention, the positioning table 520 may be conventionally assembled from two linear motion tables, one for the X direction and one of the Y direction, such as Model F55-332, and one rotary motion table, such as Model F55-327, all of which are commercially available from Edmund Industrial Optics, Barrington, N.J.

Located on top of the positioning table 520 is a support surface 522, such as a Petri dish, on which a plurality of embryos 42 are randomly oriented. The embryos 42 may be randomly placed on the support surface 522 manually by technicians or by an automated process from the manufactured seed production line.

The embryo orientation assembly 510 further includes an imaging system 524 or other suitable system for obtaining attributes of the plant embryos 42. The imaging system 524 may obtain any number of plant embryo attributes, such as size, shape, axial symmetry, cotyledon shape or development, surface texture, color, etc. In one embodiment, the imaging system 524 obtains either size or size and shape measurements, and based on these measurements, the embryos 42 will be classified as unqualified or qualified plant embryos. To be classified as a qualified embryo, the measurements of the embryo 42 should indicate, within a sufficient tolerance, that the embryo 42 fit into the cotyledon restraint opening 36 of a manufactured seed 20.

Although the use of an imaging system 524 as shown and described is preferred in one embodiment of the present invention, it should be apparent to one of ordinary skill in the art that in other embodiments, an imaging system 524 is not required. As a non-limiting example, a materials handling system formed in accordance with another embodiment of the present invention accepts all embryos, with determining whether such embryos are qualified or not. As a results, such embodiments are also within the scope of the present invention.

The aforementioned attributes are obtained by the imaging system 524 by first acquiring and then digitally storing, if necessary, images of the plant embryos 42 by a well known digital imaging camera 526. The acquired and digitally stored images are then processed by a software program executed by the computer 516 of the control system 514. The software program makes a qualitative determination of each plant embryo 42, and based on predetermined parameters, size and shape in this case, defines and stores which plant embryos are qualified, now referred to as qualified embryos 528.

In addition to processing the images taken by the digital imaging camera 526 for selected embryo attributes, the software program also determines external embryo attributes, in this case, positional information associated with each discrete qualified plant embryo 528. Since each growing medium is to receive a single qualified embryo, it will be appreciated that a selection criteria, including either size or shape and size, will disqualify groups or clusters of embryos that may be present on the support surface 522.

In an alternative embodiment, the plant embryos 42 may be qualified or otherwise determined to be suitable for germination based on other criteria, for example, surface texture, color, IR absorption or reflection, Beta ray absorption, axial symmetry, and cotyledon development or any other attribute generally measurable by camera-like sensing devices. To this end, the acquired and digitally stored images of the digital imaging camera 526 may be sent to the computer 516 of the control system 514 and may be processed by a classification software program, such as that disclosed in PCT Application No. PCT/US99/12128, entitled Method for Classification of Somatic Embryos, filed Jun. 1, 1999, the disclosure of which is hereby expressly incorporated by reference. The software program makes a qualitative determination of the plant embryos, and based on predetermined parameters, defines and stores which plant embryos are qualified.

It will be appreciated that other classification methods and systems may be practiced with the present invention for selecting qualified embryos. For example, the embryos may be classified by the multi-stage screening process disclosed in copending U.S. patent application Ser. No. 10/611,756, entitled Automated System and Method for Harvesting and Multi-Stage Screening of Plant Embryos, filed Jun. 30, 2003, the disclosure of which is hereby expressly incorporated by reference. Additionally, the embryos may be classified as qualified using a spectroscopic analysis method, such as IR spectroscopy, NIR spectroscopy, or Raman spectroscopy, as disclosed in PCT Application No. PCT/US99/12128, entitled Method for Classification of Somatic Embryos, filed Jun. 1, 1999. These classification methods may be applied to any absorption, transmittance, or reflectance spectra of the embryos to classify the embryos according to their chemical composition.

Other methods using Raman spectroscopy for classifying embryos that may be practiced with the present invention are disclosed in copending U.S. patent application Ser. No. 10/611,530, entitled Method for Classifying Plant Embryos Using Raman Spectroscopy, filed Jun. 30, 2003, the disclosure of which is hereby expressly incorporated by reference. Further, the apical dome located at the cotyledon end of a plant embryo may be three dimensionally imaged and analyzed for classifying embryos as qualified. Some methods of three-dimensionally imaging an apical dome of a plant embryo can be found in copending U.S. patent application Ser. No. 10/611,529, entitled Method and System for Three-Dimensionally Imaging an Apical Dome of a Plant, filed Jun. 30, 2003, which is hereby expressly incorporated by reference.

Based on the positional information determined for each qualified embryo 528, the qualified embryo 528 is specifically oriented one at a time by movement of the positioning table 52 to a known retrieval position for retrieval by the transfer system 512. The qualified embryo 528 is then retrieved by the transfer assembly 512, and subsequently inserted into a seed shell 24, as will be described in detail below. In the embodiment shown, the qualified embryos 528 are sequentially orientated at the retrieval position so that each qualified embryo 528 may be grasped with its cotyledon end aligned in the X direction, as best shown in FIG. 6.

In accordance with one aspect of the present invention, the queuing order in which the qualified embryos 528 are selected for retrieval may be specifically determined for improving the throughput of the embryo delivery process. The retrieval order of the qualified embryos 528 from the support surface 522 may be determined by any number of throughput enhancement routines. In the preferred embodiment, the throughput enhancement routine is executed by the computer 516, which sorts the positional information obtained by the imaging system 524 and processed by the computer 516 to select the retrieval order of qualified embryo 528 based on the relative positions of the qualified embryos 528.

In operation, the routine first sorts all qualified embryos 528 by rotational position starting with the qualified embryo that has a rotational position, in either degrees or radians, closest to a defined reference position, such as the default positional setting of the position table. Next, the routine controls the positioning table 520 to sequentially orient the qualified embryo 528 to be retrieved by the transfer assembly 512 according to the sorted rotational position information.

Referring to FIG. 5, the transfer assembly 512 will now be described in greater detail. The transfer assembly 512 includes a transfer device 540 selectively movable in a guided manner along a track 542. The selective movement of the transfer device 540 may be effected by any well known linear actuator (not shown), such as a motorized linear screw or a pneumatic piston and cylinder arrangement, and controlled by the control system 514. The transfer device 540 may include a housing 544 having a motorized rotary shaft 546 extending from the housing 544 in the Y direction.

The rotary shaft 546 is selectively rotatable between the retrieval position shown in phantom in FIG. 5 (farthest to the left) and the release position, as shown farthest to the right in FIG. 5. Attached to the rotary shaft 546 for rotational movement therewith is an extension member 548. Attached at the distal end of the extension member 548 are microtweezers 550.

As best seen in FIG. 6, the microtweezers 550 include arms 552 to which microtweezer tips 554 ("tips 554") are attached. The tips 554 are preferably attached to the arms 552 at an angle, for example, 30 degrees, to facilitate the retrieval and release of the qualified embryos 528. The microtweezers 550 may be fabricated out of silicon in an etching or similar process. It will be appreciated that silicon at the contemplated dimensions is capable of flexing.

The tips 554 are movable between an open position (shown in phantom in FIG. 6), wherein space between the tips 554 is sufficient to accept a qualified embryo 528 therebetween, and a closed position, wherein the tips 554 grasp the qualified embryo 528. The tips 554 are configured to create a contact surface sized to minimize the effects of surface tension created by the moisture of the embryo contacting the tips 554. In particular, the tips 554 are designed with a suitable contact area the allows the release of the qualified embryo 528 when the microtweezers 550 are actuated to the open position, and will minimize the manipulation or movement of the qualified embryo 528 prior to release.

In one embodiment, the contact area is sized such that when the microtweezers 550 are actuated to release the qualified embryo 528, the weight of the qualified embryo 528 overcomes the surface tension therebetween, which in turn, separates the qualified embryo 528 from the microtweezers 550. In another embodiment, the contact area on each tip 554 is approximately 10-100 microns in width, and approximately 2 mm in height. It will be appreciated that only a small portion of the 2 mm height will actually contact the embryo, preferably at the distal end, due to the size, shape, and surface curvature of the embryo. Microtweezers that may be practiced by the present invention are commercially available from MEMS Precision Instruments (http://www.memspi.com).

In operation, once the positioning table 520 orients one qualified embryo 528 into the retrieval position, the transfer assembly 512 retrieves the qualified embryo 528. To do so, the transfer device 540 is translated along the track 542 and the microtweezers 550 are rotated by the rotary shaft 546 to the retrieval position, shown in phantom in FIG. 4. The microtweezers 550 may be rotated into the retrieval position contemporaneously with the movement of the transfer device 540 or rotated to the retrieval position subsequent to the movement of the transfer device 540.

Once the retrieval position has been achieved, the microtweezers 550 are actuated from the open position, shown in phantom in FIG. 6, to the closed position for grasping the qualified embryo 528. The microtweezers 550 may be actuated to the closed position in a number of different methods; however, in the preferred embodiment, the microtweezers 550 are actuated to the closed position by the application of electrical current to the arms 552 as known in the art, and controlled by the computer 516. Similarly, the microtweezers 550 may be actuated to the open position, when desired, by shutting off the application of electrical current to the arms 552, as known in the art.

After the qualified embryo 528 is retrieved from the support surface 522, the transfer device 540 is translated along the track 542 to a second, release position, while contemporaneously rotating the shaft 546 in the direction shown by the arrow 556 and opposite of the retrieval direction. Due to the small size of the microtweezers 550 and the qualified embryo 528 to be retrieved, the imaging camera 526 may be operated continuously to provide feedback control information for repositioning the positioning table 520 and/or controlling the actuation of the microtweezers 550 via the computer 516.

While the transfer device 540 is shown linearly translating along the track 542, it will be appreciated that other methods for transferring the qualified embryos 528 from the retrieval position to the release position are possible. For example, the transfer device 540 may employ a robotic swing arm that rotates about the Z-axis for moving the microtweezers 550 between such known positions. Additionally, it will be appreciated that the housing 544 may be a robotic housing capable of movement in the X, Y, and Z directions, as well as rotating about the Z-axis. The robotic housing of such a transfer device may be used in conjunction with or in the absence of the positioning table 520 for positioning the microtweezers 550 to retrieve the selected qualified embryos 528.

Figure 7:
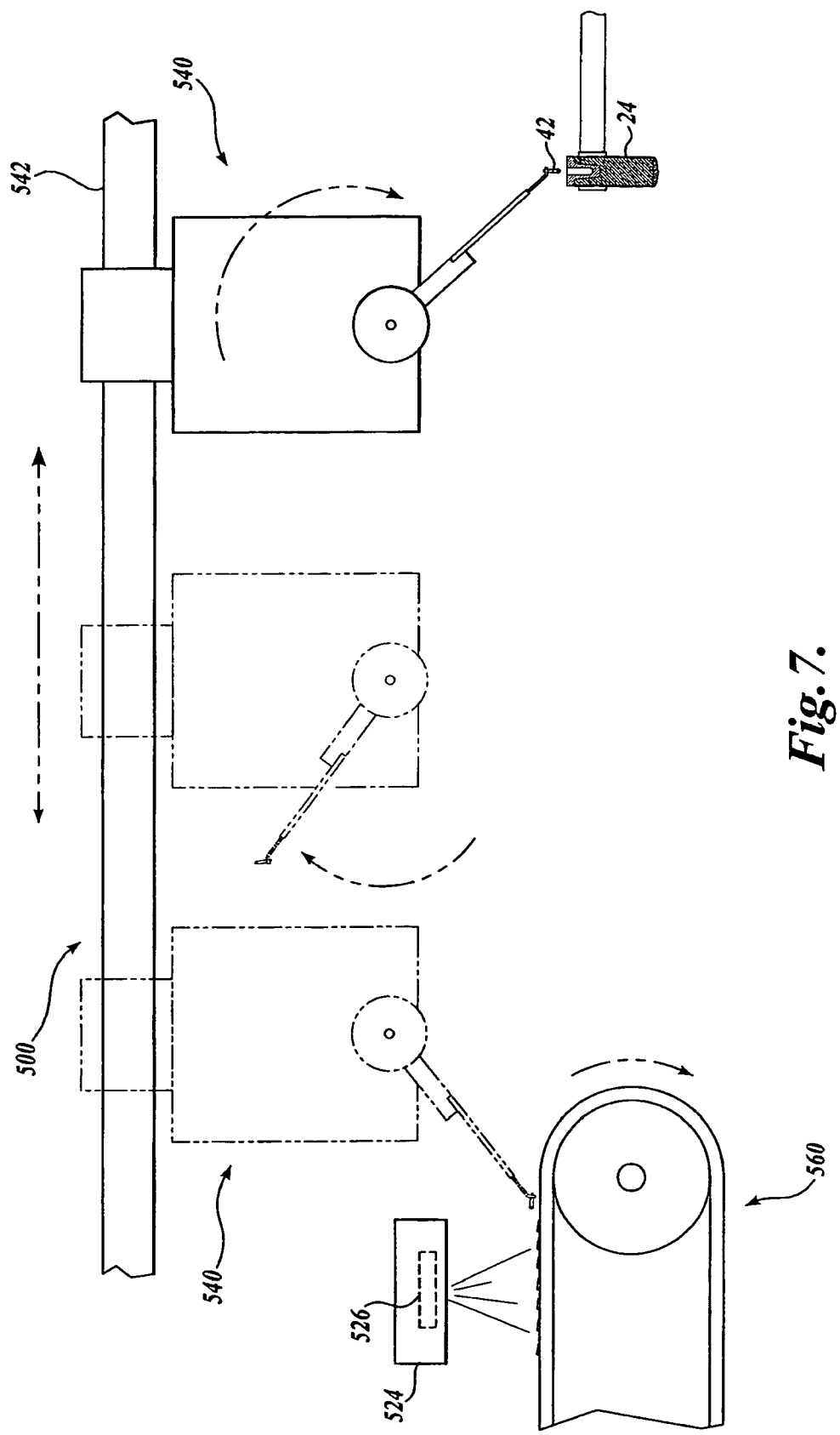
FIG. 7 is an embryo delivery system constructed in accordance with an alternate embodiment of the present invention.
Figure 8:
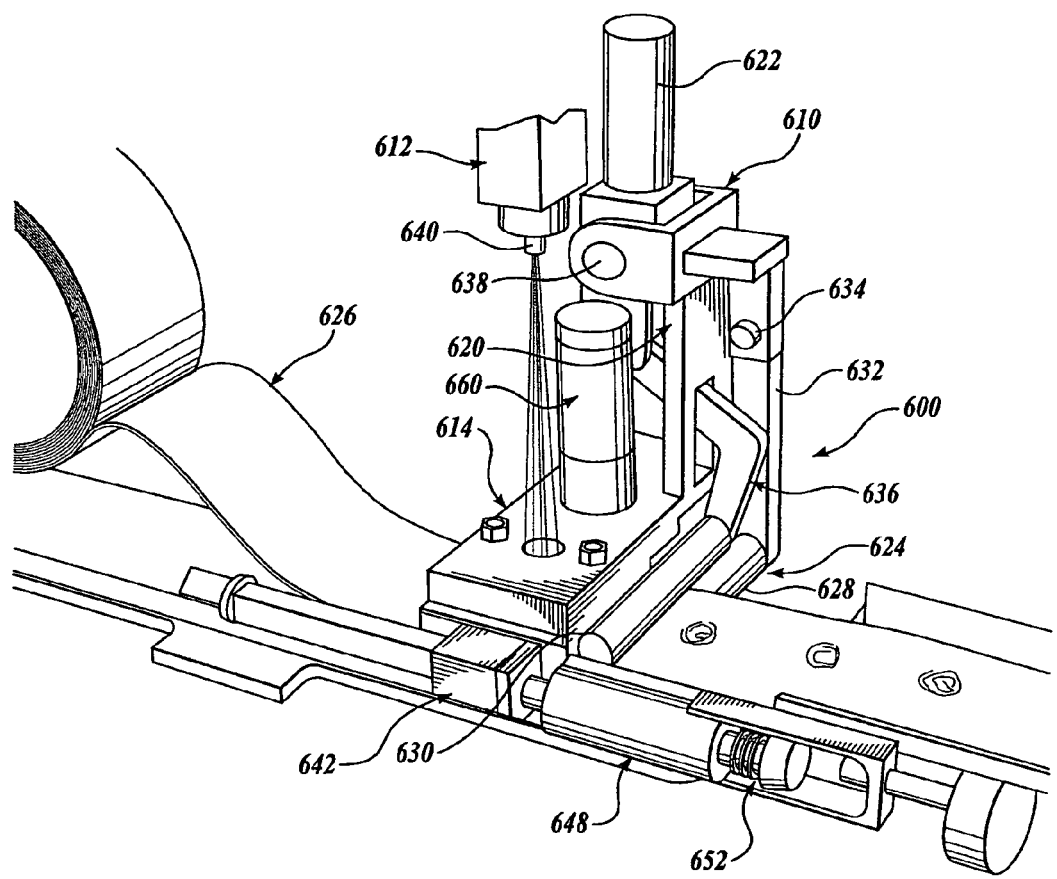
FIG. 8 is a perspective view of an apparatus used to manufacture and attach an end seal to a manufactured seed in accordance with various embodiments of the present invention.

While the orientation assembly 510 in the embodiment shown in FIG. 5 and described herein employ a positioning table 520, it will be appreciated that other orientation assemblies may be used. For example, as best shown in FIG. 7, the embryos may be retrieved off of a conventional conveyor belt 560. In this embodiment, either the embryos are pre-oriented on the conveyor belt 560 to be grasped by the transfer assembly 512 disclosed herein, or the transfer assembly 512 may employ a multi-directional and rotational robotic housing for orienting the microtweezers 550 with respect the qualified embryos 528. Additionally, the embryo delivery system 500 may employ the orientation and imaging system disclosed in PCT Application No. PCT/US00/40720 (WO 01/13702 A2), which is expressly incorporated by reference, for positioning the qualified embryos 528 in a sufficient orientation at the retrieval position.

Further, it will be appreciated that the qualified embryo does not have to be directly inserted into the manufactured seed coat at the release position described above. Instead, the qualified embryo may be inserted into a temporary carrier, or could be released onto a different surface in a desired location or orientation. The surface may be a temporary storage location, or a movable surface, such as a conveyor belt, movable web, or positioning table, to name a few.

Figure 4:
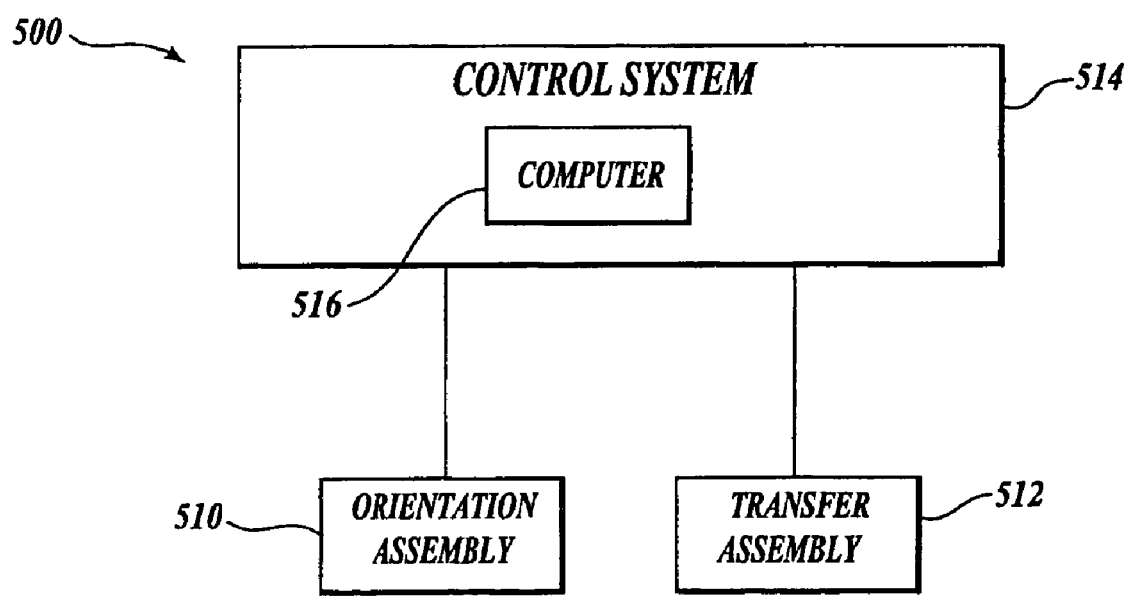
FIG. 4 is a block diagram depicting the components of an embryo delivery system for the materials handling system of FIG. 2.

Operation of the embryo delivery system 500 may be best understood by referring to FIGS. 4-6. A plurality of embryos 42 are delivered from the Embryogenesis production line, either manually or by an automated process, and are randomly placed on the support surface 522 of the positioning table 520. Next, the imaging camera 526 acquires and digitally stores, if necessary, images that will be used to determine whether any of the embryos 42 can be considered qualified to be placed in seed shell 24.

If the embryos 42 are qualified to be placed in a manufactured seed, the positional information of each qualified embryo 528 is determined and is used to assemble an embryo retrieval queue. In one embodiment of the present invention, the qualified embryos 528 are sorted and arranged in the queue by rotational coordinate information. Once the control system 514 generates a retrieval queue, whether using a throughput enhancement routine or not, the first qualified embryo 528 is oriented by the positioning table 520, through control signals sent by the control system 514, to the precise retrieval position.

Contemporaneously with or sequentially after orientating the qualified embryo 528 to the retrieval position, the control system 514 sends controls signals to the transfer device 540 such that the transfer device 540 translates to the retrieval position and the rotary shaft 546 rotates the microtweezers 550 in the direction opposite the arrow 556 to the embryo retrieval position. Once the microtweezers 550 are in the retrieval position, they are actuated to the closed position, thereby grasping the qualified embryo 528 between the tips 554.

In one embodiment, to improve the accuracy of the retrieval process and to ensure that the tweezers have retrieved a qualified embryo 528, the imaging system 524 may be continuously acquiring images of the position of the tips 554 with respect to the qualified embryo 528, for providing feedback control information to the computer 516.

After the qualified embryo 528 is retrieved from the support surface 522, the transfer device 540 is translated in the opposite direction along the track 542 to the release position, while contemporaneously rotating the shaft 546 in the opposite direction shown by the arrow 556. Once the qualified embryo 528 in aligned with the cotyledon restraint opening 36, the microtweezers 550 are actuated by the control system 514 to the open position, thereby releasing the qualified embryo 528 into the seed shell 24.

As was described above, the tips 554 of the microtweezers 550 are configured to reduce the contact area against the qualified embryo 528. As such, the weight of the qualified embryo 528 overcomes the surface tension generated between the moist qualified embryo 528 and the contact area of the tips 554, thereby releasing the qualified embryo 528 from the microtweezers 550 and depositing the embryo into the seed shell 24. Thereafter, the transport assembly 100 is actuated to rotate the seed shell 24 in a direction indicated by the arrow 590 and move the seed shell 24 containing the embryo to the live end seal formation assembly 600.

The live end seal formation assembly 600 ("end seal assembly 600") used in the formation and attachment of an end seal 44 to a manufactured seed 20 is best seen by referring to FIGS. 8-14. The end seal assembly 600 includes a sealing material advancement assembly 610, a sealing assembly 612, and an end seal formation and attachment assembly 614.

The sealing assembly advancement assembly 610 includes a frame 620, a pneumatic cylinder 622, advancement rollers 624, and a source of sealing material 626. The pneumatic cylinder 622 is operatively connected to the advancement rollers 624. The advancement rollers 624 include first and second roller bars 628 and 630. The first roller bar 628 is attached to a first pivot link 632 and is pivotably connected to the frame 620 at a first pivot point 634. The second roller bar 630 is connected to one end of a second pivot link 636 and pivots about a second pivot point 638 for selective advancement of the sealing material 626.

In the illustrated embodiment, the sealing material 626 is pinned between opposing surfaces of the first and second roller bars 628 and 630. After formation of the end seal 44, as is described in greater detail below, the pneumatic cylinder 622 is actuated to selectively advance the sealing material 626 relative to the end seal formation and attachment assembly 614 by pivoting the first and second pivot links 632 and 636 about their respective pivot points 634 and 638.

The sealing assembly 612 is a well-known heat generator, such as a laser, and includes an emitter 640. The sealing assembly 612 is disposed above the end seal formation and attachment assembly 614 and is positioned to seal and cut the end seal 44 to a manufactured seed 20, as is described in greater detail below.

Still referring to FIGS. 8-12, the end seal formation and attachment assembly 614 will now be described in greater detail. The end seal formation and attachment assembly 614 includes a blower assembly 642, a clamping assembly 644, and a main cylinder 646. The blower assembly 642 includes a pneumatically operated cylinder 648 in fluid communication with a first air passageway 650 extending through a portion of the blower assembly 642. The blower assembly 642 may include a volume control assembly 652. The volume control assembly 652, which is suitably a torque thumb screw, selectively sets the amount of fluid within the cylinder 648 used in the process of creating the end seal 44. In that regard, by adjusting the volume control assembly 652, the volume within the cylinder 648 is either increased or decreased, thereby controlling the volume of air used in the creation of the end seal 44.

Figure 9:
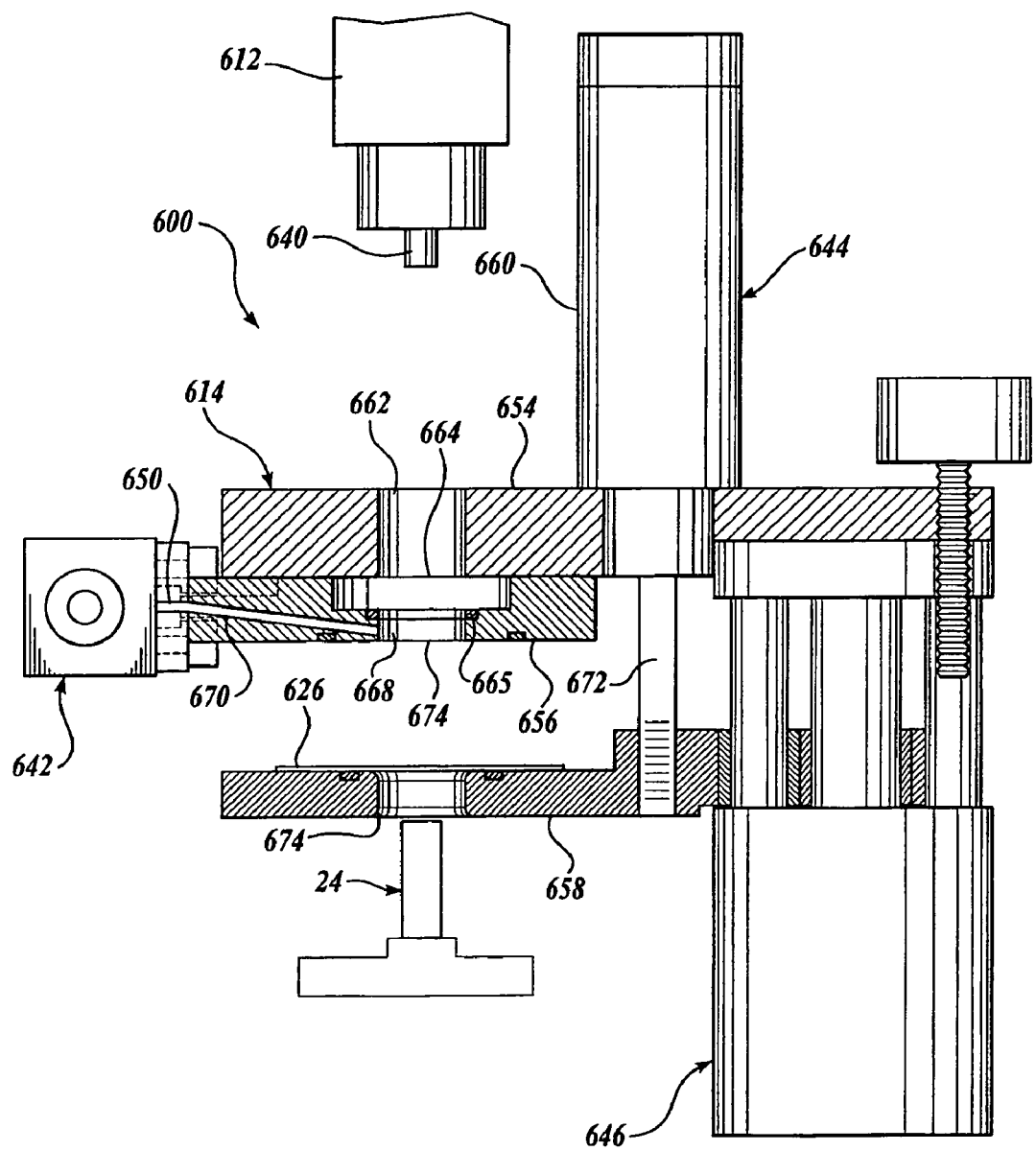
FIG. 9 is a cross-sectional, side planar view of the apparatus of FIG. 8, showing the apparatus in an open position.

As may be best seen by referring to FIG. 9, the clamping assembly 644 includes a top plate 654, a lens plate 656, and a clamp plate 658 operatively connected to a clamp cylinder 660. The top plate 654 is substantially rectangular in configuration and includes a bore 662 extending therethrough. The bore 662 is positioned below emitter 640 of the sealing assembly 612 and is suitably located adjacent the lens plate 656.

The lens plate 656 includes, in one embodiment, a laser lens 664 seated within a cavity extending partially through the lens plate 656. A suitable O-ring 665 seals the laser lens 664 within the cavity of the lens plate 656. The lens plate 656 also includes a bore 668 extending between the lower surface of the cavity and the lower surface of the laser plate 656. The bore 668 is also in fluid communication with a second air passageway 670 extending between the bore 668 and a side of the lens plate 656. The second air passageway 670 is in fluid communication with the first air passageway 650 of the blower assembly 642.

The clamp plate 658 is connected to a piston 672 of the clamp cylinder 660. The clamp plate 658 is suitably a rectangular member and also includes a bore 674 extending through the clamp plate 658. The sealing material 626 is suitably located on the clamp plate 658 and is located above the bore 674.

Figure 10:
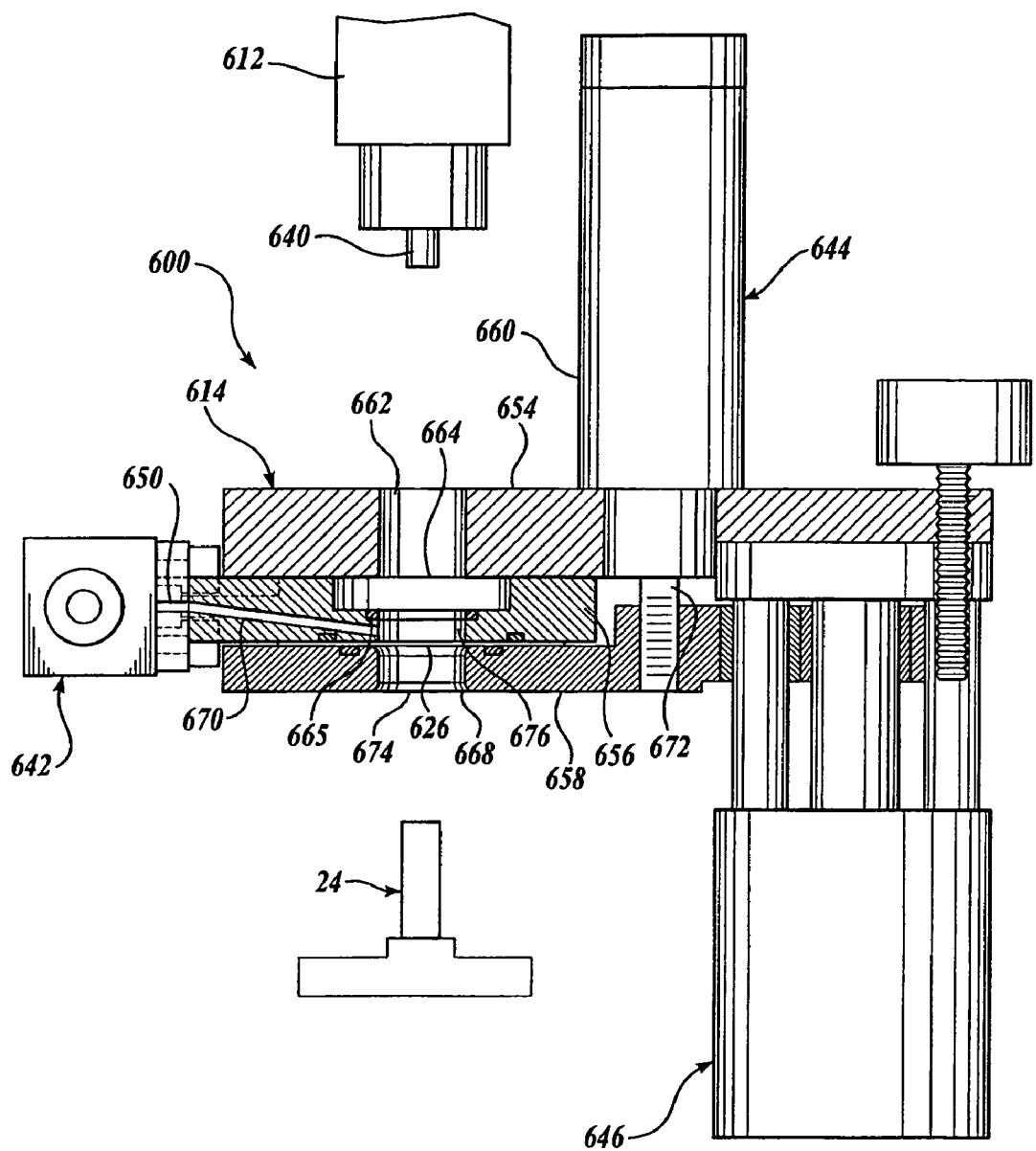
FIG. 10 is a cross-sectional, side planar view of the apparatus of FIG. 9, showing a portion of the apparatus in a clamped position.
Figure 11:
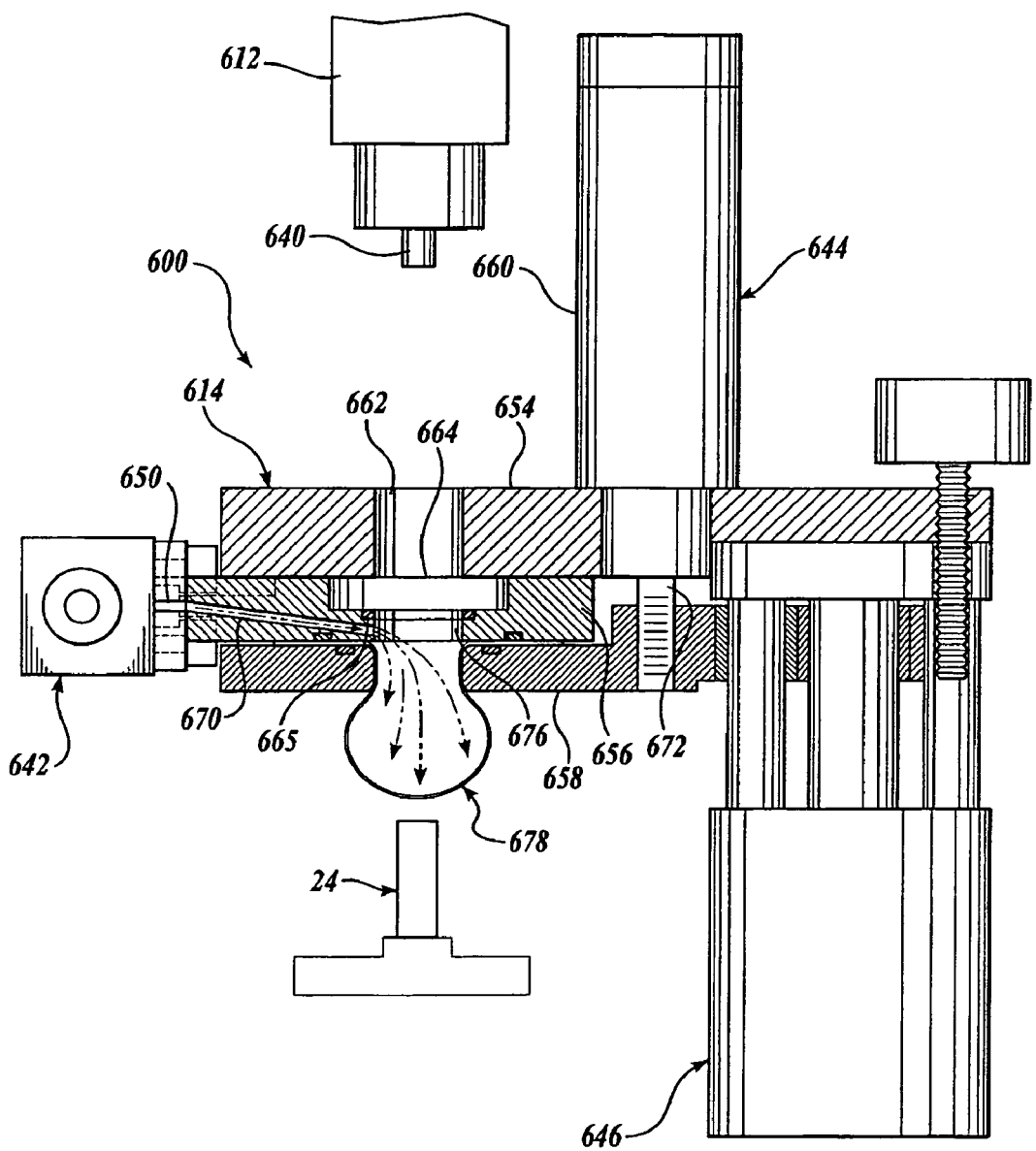
FIG. 11 is a cross-sectional, side planar view of the apparatus of FIG. 10, showing the formation of an enclosure in accordance with certain embodiments of the present invention.

As may be best seen by referring to FIG. 10, when the clamping assembly 644 is displaced into the clamped position, the clamp plate 658 is urged upwardly against the lower surface of the lens plate 656, such that a sealed chamber 676 is formed by the lower surface of the laser lens 664 and the upper surface of the sealing material 626. After the sealing material 626 is clamped between the lens plate 656 and the clamp plate 658, air is transferred from the blower assembly 642 through the first and second air passageways 650 and 670 to form an enclosure 678, as seen in FIG. 11.

The enclosure 678 is bubble-like in configuration and is created by the in-flow of air into the chamber 676. As air is dispensed into the chamber 676, the pressurization causes the sealing material 626 to stretch and thin in the area of the sealing material 626 forming the enclosure 678. Specifically, as the enclosure 678 expands or inflates, the thickness of the sealing material 626 thins to a predetermined burst strength. At this predetermined burst strength, and after the enclosure 678 is attached to the manufactured seed 20 to form the end seal 44, an embryo 42 germinating within the cavity 34 of the manufactured seed 20 will break through the end seal 44 at the desired burst strength. Verification of the burst strength is obtained by well-known penetrometers.

Although it is preferred that air is the preferred medium to create the enclosure 678, it should be apparent that other fluid or gaseous media are also within the scope of the present invention. As a nonlimiting example, the medium used to create the enclosure 678 also includes liquids, such as water. Further, as used within the context of the present invention, the term "enclosure" includes not only bubble-like structures, but also any equivalent structure, such as a preformed cap made from the sealing material 626 or similar material. Accordingly, such enclosures are also within the scope of the present invention.

Figure 12:
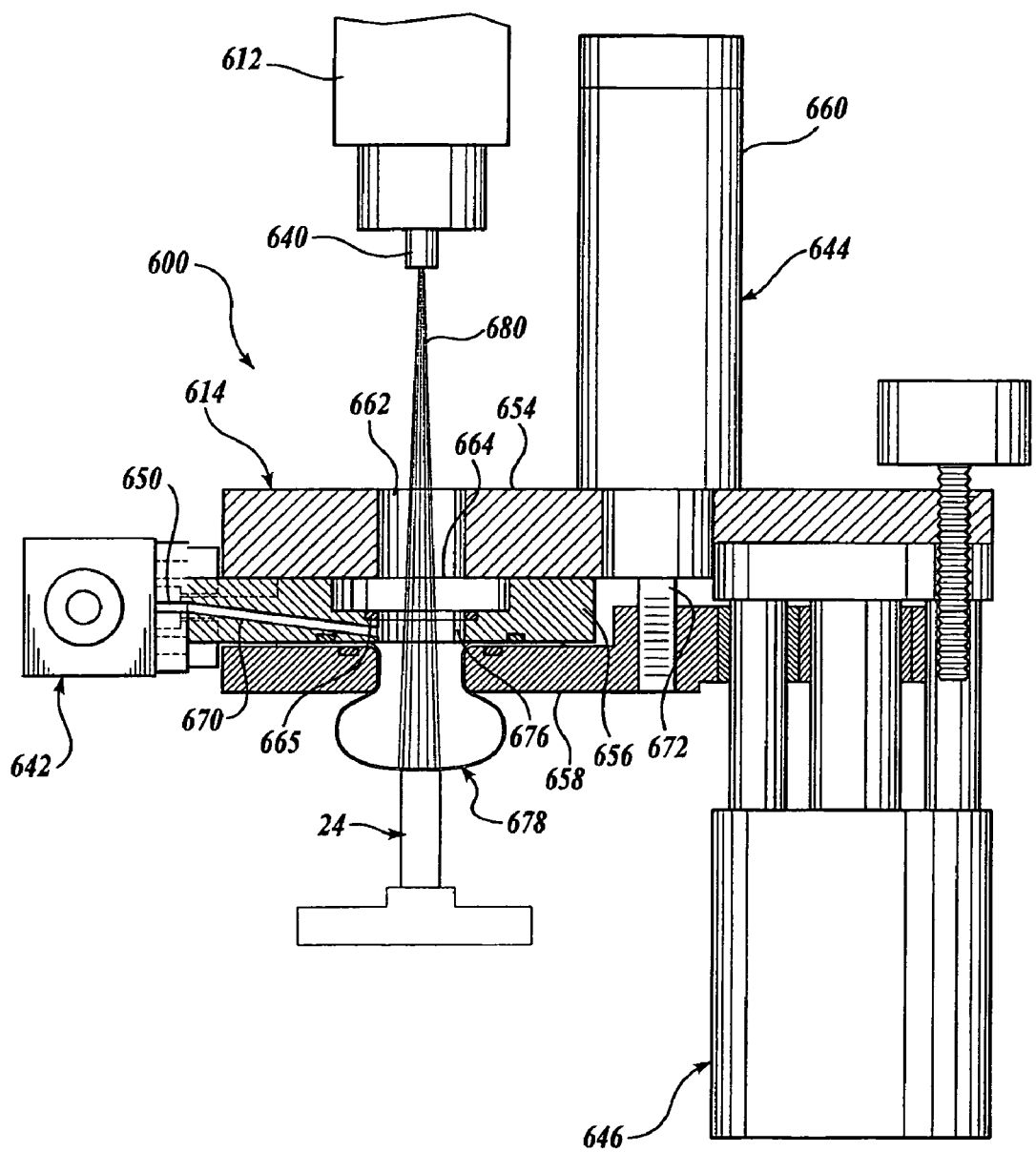
FIG. 12 is a cross-sectional, side planar view of the apparatus of FIG. 11, showing attachment of an enclosure to a manufactured seed in accordance with one embodiment of the present invention.

As may be best seen by referring to FIG. 12, after the enclosure 678 is formed, the main cylinder 622 selectively displaces the enclosure 678 into contact with the seed shell 24. Thereafter, a heat source 680 is applied to an interior surface of the enclosure 678 to seal a portion of the enclosure 678 to the seed shell 24, thereby forming the end seal 44. Suitably, the heat source 680 may also simultaneously or sequentially cut a disk-shaped portion of the enclosure 678 as it seals it to the seed shell 24.

In one embodiment of the present invention, the heat source 680 is suitably a laser beam from a well-known laser.

As previously noted, it should be apparent that other heat sources, such as devices that fuse the enclosure 678 to the seed shell 24, are also within the scope of the present invention. Further still, it should be apparent to one of ordinary skill in the art that the main cylinder 622 may either selectively displace the enclosure 678 into contact with the seed shell 24, or move the seed shell 24 into contact with the enclosure 678. Accordingly, such embodiments are also within the scope of the present invention.

A summary of the method of the present embodiment is best understood by referring to FIGS. 8-12. In that regard, a sheet of sealing material 626 is clamped between a clamp plate 658 and a lens plate 656. A predetermined volume of fluid fills a chamber 676 formed by the bore 668 and the upper surface of the sealing material 626. As the predetermined volume of fluid is dispensed into the chamber 676, a portion of the sealing material 626 expands to form an enclosure 678. As the enclosure 678 is formed, it reduces the thickness of the sealing material 626 forming the enclosure to a substantially constant thickness. As a result, the enclosure 678 has a predetermined burst strength.

After the formation of the enclosure 678, it is selectively displaced into contact with a seed shell 24. Thereafter, a heat source 680 is applied to an interior surface of the enclosure 678 to seal and cut away a portion of the enclosure 678, thereby forming an end seal 44. It should be apparent to one of ordinary skill in the art that the predetermined volume of fluid used to form the enclosure 678 to achieve the preferred burst strength is a function of the type of sealing material 626 selected to form the enclosure 678. As a nonlimiting example, for Parafilm®, a preferred volume of fluid is between 1.96 mm$^3$ and 6,642 mm$^3$. In another nonlimiting example, the predetermined volume is suitably 25.25 mm$^3$.

Figure 13:
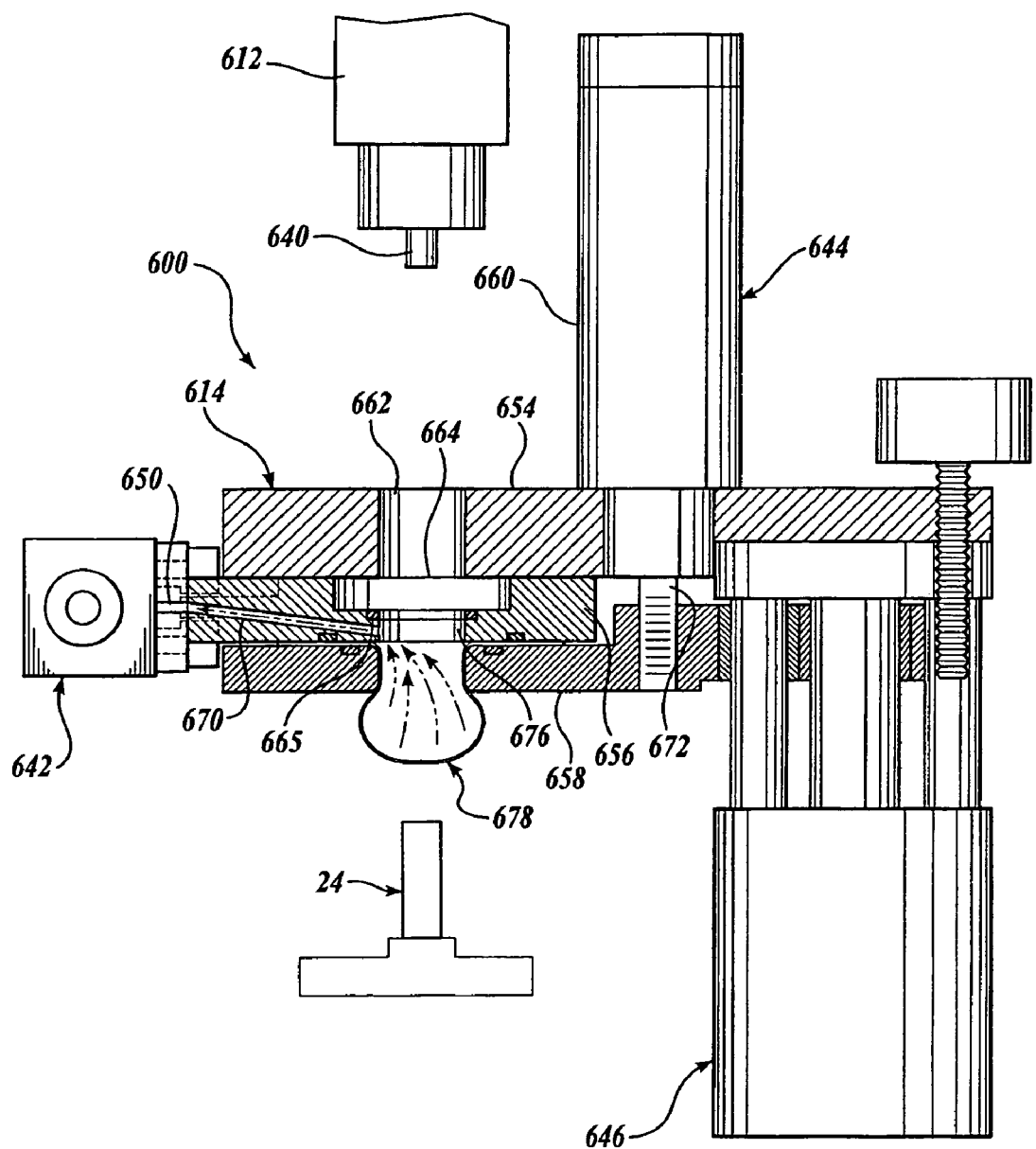
FIG. 13 is a cross-sectional, side planar view of the apparatus of FIG. 10, showing the formation of an enclosure in accordance with another embodiment of the present invention.
Figure 14:
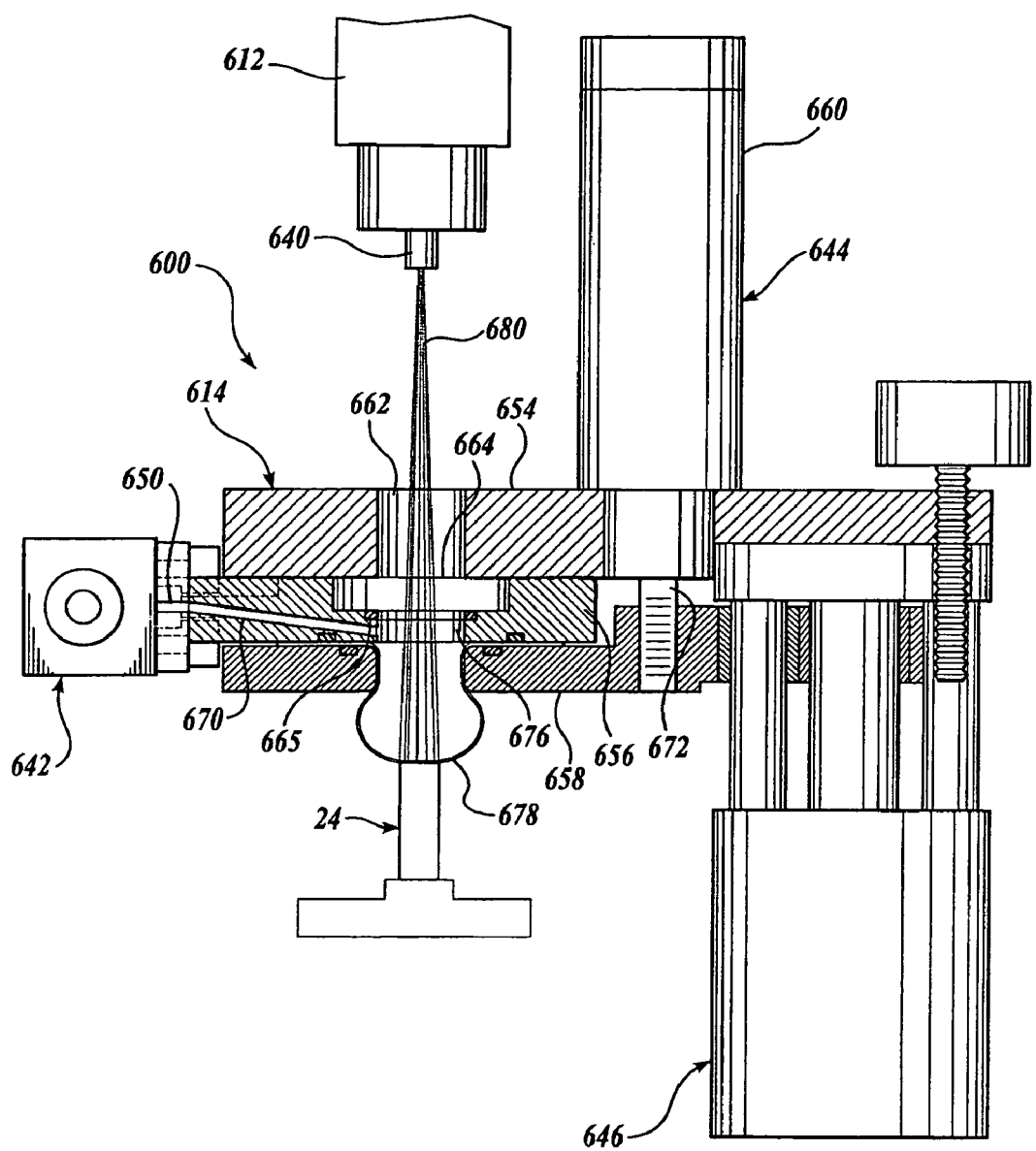
FIG. 14 is a cross-sectional, side planar view of the apparatus of FIG. 13, showing the attachment of an enclosure to a manufactured seed in accordance with another embodiment of the present invention.

Referring now to FIGS. 13 and 14, an alternate embodiment of forming and attaching an end seal 44 in accordance with the present invention will now be described in greater detail. All apparatuses and materials described above for the first embodiment are identical for the present embodiment with one notable difference. Specifically, forming an enclosure 678 in accordance with the present embodiment includes forming an enclosure 678 by providing a first volume of air, waiting a predetermined period of time, and then allowing a portion of the first volume of air to exhaust out from the enclosure 678 to define a predetermined second volume of air within the enclosure 678. Thereafter, a portion of the enclosure 678 is sealed and attached to the seed shell 24 in a manner described above and shown in FIG. 14.

Thus, the present embodiment includes dispensing a predetermined first volume of fluid into the enclosure 678. The first volume of fluid is between the range of 1600 mm$^3$ to 8200 mm$^3$. Then, wait a predetermined period of time. This predetermined period of time is suitably between a range of one second to 20 seconds. As a specific, nonlimiting example, the predetermined period of time is three seconds. Thereafter, a predetermined portion of fluid is extracted from within the enclosure 678 to define a second volume of air, suitably between the range of 0 mm$^3$ to 6600 mm$^3$.

As a specific example of the present embodiment, the enclosure 678 is inflated with a first volume of air equal to approximately 3300 mm$^3$. After three seconds, approximately 820 mm$^3$ of air is removed, thereby leaving a second volume of fluid of approximately 2480 mm$^3$ within the enclosure 678. Then, the enclosure 678 is displaced into contact with and sealed to the manufactured seed as described above for the previous embodiments.

After the seed shell 24 is sealed at the live end seal formation assembly 600, the transport assembly 100 (FIG. 2) is actuated to move the seed shell 24, now known as a manufactured seed 20, to the seed removal assembly 700. The seed removal assembly 700 includes a robotic arm 710 and a seed receptacle 712. One end of the robotic arm 710 includes a clamp 714. The clamp 714 is sized and positioned to selectively grasp the manufactured seed 20 from the transport assembly 100. This is suitably accomplished by the robotic arm rotating to a position where the clamp 714 is adjacent the clamp 122 of the transport assembly 100. At this position, the manufactured seed 20 is transferred to the seed removal assembly 700.

After the robotic arm 710 receives the manufactured seed 20, it is actuated in a suitable pivoting motion to position the manufactured seed 20 for placement on the seed receptacle 712. In the embodiment of FIG. 2, the seed receptacle 712 is a conveyor belt. Although a conveyor belt is illustrated as one embodiment of the seed receptacle, it should be apparent that the invention is not intended to be so limited. As a non-limiting example, the seed receptacle 712 may be bucket or some other container sized and positioned to receive a manufactured seed. As a result, such embodiments are also within the scope of the present invention.

Figure 15:
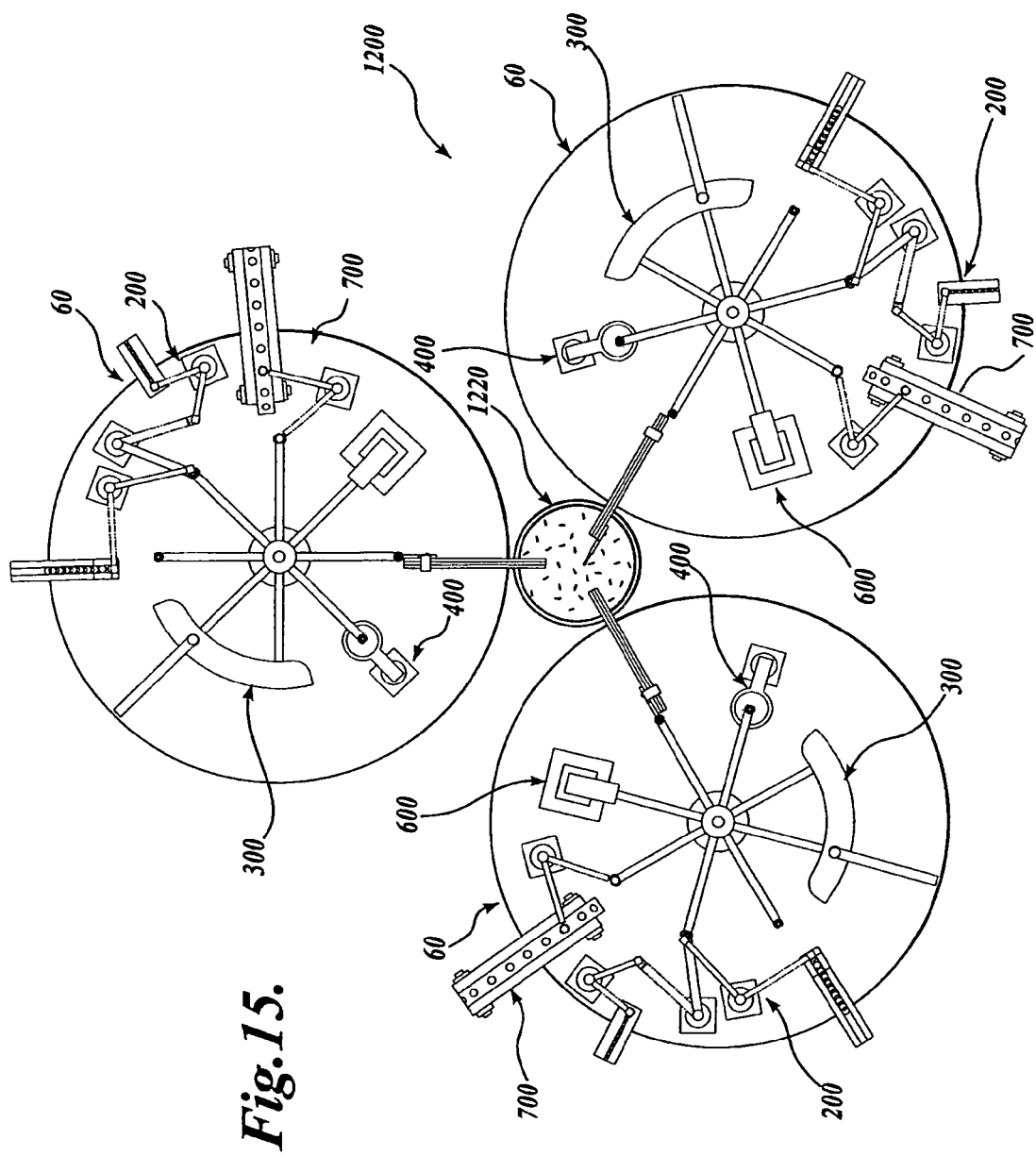
FIG. 15 is a top planar view of a materials handling system constructed in accordance with another embodiment of the present invention.

Referring now to FIG. 15, a materials handling system 1200 formed in accordance with another embodiment of the present invention will now be described in detailed. The materials handling system 1200 of the present embodiment is identical in materials and operation as the first embodiment described above with respect to FIGS. 1-14 with the exception as follows. In that regard, the materials handling system 1200 includes a plurality of materials handling systems 60 each retrieving embryos from a centrally located embryo plate 1220. Specifically, the illustrated embodiment includes a total of three materials handling systems 60. Such an arrangement is beneficial as it allows a plurality of materials handling systems to simultaneously retrieve embryos.

Although an embryo plate 1220 is preferred, it should be apparent that the invention is not intended to be so limited. As a non-limiting example, a conveyor belt apparatus supplying embryos to each of the materials handling systems 60 is alternate embodiment. Accordingly, other embodiments are also within the scope of the present invention.

Although a total of three materials handling systems 60 are illustrated in FIG. 15, it should be apparent that embodiments having fewer or greater materials handling systems, such as two, four, five, ten, etc., are also within the scope of the present invention.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. In a material handling system having means for automatically assembling and transporting an artificial seed between a plurality of assembly stations arranged in a substantially sequential configuration, a method of manufacturing an artificial seed comprising:
   (a) transporting a seed shell to a media fill station by a transport assembly that transports the seed shell between a plurality of assembly stations;
   (b) depositing media into the seed shell;
   (c) sealing the media within one end of the seed shell;
   (d) depositing an embryo within the seed shell; and
   (e) sealing the embryo within the seed shell.

2. The method of manufacturing an artificial seed of claim 1, further comprising coupling a seed shell with a restraint prior to transporting a seed shell to a media fill station.

3. The method of manufacturing an artificial seed of claim 2, further comprising placing a restraint on a receptacle prior to coupling a seed shell with a restraint.

4. The method of manufacturing an artificial seed of claim 1, further comprising causing the media to change state.

5. The method of manufacturing an artificial seed of claim 4, wherein causing the media to change state includes cooling the seed shell.

6. The method of manufacturing an artificial seed of claim 5, wherein cooling the seed shell occurs after depositing media into the seed shell.

7. The method of manufacturing an artificial seed of claim 1, further comprising rotating the seed shell prior to sealing the media within one end of the seed shell.

8. The method of manufacturing an artificial seed of claim 1, further comprising transferring a seed from a transport assembly to a seed removal assembly after sealing the embryo within the seed shell.

9. The method of manufacturing an artificial seed of claim 1, wherein sealing the media within one end of the seed shell includes dipping the seed shell in a container of end seal formation material.

* * * * *